US009499860B2

(12) United States Patent
Kankia

(10) Patent No.: US 9,499,860 B2
(45) Date of Patent: Nov. 22, 2016

(54) PRIMERS AND METHODS FOR NUCLEIC ACID AMPLIFICATION

(75) Inventor: Besik Kankia, Columbus, OH (US)

(73) Assignee: The Ohio State University, Columbus, OH (US)

( * ) Notice: Subject to any disclaimer, the term of this patent is extended or adjusted under 35 U.S.C. 154(b) by 0 days.

(21) Appl. No.: 13/579,486

(22) PCT Filed: Feb. 18, 2011

(86) PCT No.: PCT/US2011/025411
§ 371 (c)(1),
(2), (4) Date: Aug. 16, 2012

(87) PCT Pub. No.: WO2011/103407
PCT Pub. Date: Aug. 25, 2011

(65) Prior Publication Data
US 2012/0315642 A1 Dec. 13, 2012

Related U.S. Application Data

(60) Provisional application No. 61/338,475, filed on Feb. 19, 2010.

(51) Int. Cl.
*C12Q 1/68* (2006.01)
(52) U.S. Cl.
CPC ........... *C12Q 1/6844* (2013.01); *C12Q 1/6816* (2013.01)
(58) Field of Classification Search
CPC .................................................. C12Q 1/6844
USPC ............................................. 435/6.12, 91.2
See application file for complete search history.

(56) References Cited

U.S. PATENT DOCUMENTS

| 4,683,195 A | 7/1987 | Mullis et al. | |
|---|---|---|---|
| 4,683,202 A | 7/1987 | Mullis | |
| 5,691,145 A | 11/1997 | Pitner et al. | |
| 6,277,605 B1 * | 8/2001 | Wijnhoven et al. | 435/91.2 |
| 6,316,200 B1 | 11/2001 | Nadeau et al. | |
| 7,223,536 B2 * | 5/2007 | Wright et al. | 435/6.1 |
| 7,517,644 B1 | 4/2009 | Smith | |
| 7,618,814 B2 * | 11/2009 | Bentwich | 435/320.1 |
| 7,807,648 B2 * | 10/2010 | Kmiec et al. | 514/44 R |
| 8,034,568 B2 | 10/2011 | Kurn et al. | |
| 8,329,404 B2 | 12/2012 | McKernan et al. | |
| 2001/0009761 A1 * | 7/2001 | Wright et al. | 435/6 |
| 2001/0039040 A1 * | 11/2001 | Wijnhoven et al. | 435/91.1 |
| 2004/0115706 A1 * | 6/2004 | Jin et al. | 435/6 |
| 2009/0017009 A1 * | 1/2009 | Bates et al. | 424/130.1 |

FOREIGN PATENT DOCUMENTS

| EP | 0684315 A1 | 11/1995 |
|---|---|---|
| WO | 2009079215 A1 | 6/2009 |
| WO | 2009143476 A2 | 11/2009 |
| WO | 2012129263 A2 | 9/2012 |

OTHER PUBLICATIONS

Fletcher TM, Sun D, Salazar M, Hurley LH. Effect of DNA secondary structure on human telomerase activity. Biochemistry. Apr. 21, 1998;37(16):5536-41.*
Xu Y, Sugiyama H. Formation of the G-quadruplex and i-motif structures in retinoblastoma susceptibility genes (Rb). Nucleic Acids Res. Feb. 7, 2006; 34(3):949-54. Print 2006.*
Chou SH, Chin KH, Wang AH. DNA aptamers as potential anti-HIV agents. Trends Biochem Sci. 2005. 30(5):231-4.*
Gomez D, Mergny JL, Riou JF. Detection of telomerase inhibitors based on g-quadruplex ligands by a modified telomeric repeat amplification protocol assay. Cancer Res. Jun. 15, 2002;62(12):3365-8.*
Han H, Hurley LH, Salazar M. A DNA polymerase stop assay for G-quadruplex-interactive compounds. Nucleic Acids Res. Jan. 15, 1999;27(2):537-42.*
Johnson J, Okyere R, Joseph A, Musier-Forsyth K, Kankia B. Quadruplex formation as a molecular switch to turn on intrinsically fluorescent nucleotide analogs. Nucleic Acids Res. Jan. 7, 2013;41(1):220-8.*
Kankia BI. A real-time assay for monitoring nucleic acid cleavage by quadruplex formation. Nucleic Acids Res. 2006;34(20):e141. Epub Oct. 28, 2006.*
Kankia BI. Self-dissociative primers for nucleic acid amplification and detection based on DNA quadruplexes with intrinsic fluorescence. Anal Biochem. Feb. 1, 2011;409(1):59-65.*
Kelley S, Boroda S, Musier-Forsyth K, Kankia BI. HIV-integrase aptamer folds into a parallel quadruplex: a thermodynamic study. Biophys Chem. May 2011;155(2-3):82-8.*
Kwok CK Sherlock ME, Bevilacqua PC. Effect of loop sequence and loop length on the intrinsic fluorescence of G-quadruplexes. Biochemistry. May 7, 2013;52(18):3019-21.*
Liu JQ, Chen CY, Xue Y, Hao YH, Tan Z. G-quadruplex hinders translocation of BLM helicase on DNA: a real-time fluorescence spectroscopic unwinding study and comparison with duplex substrates. J Am Chem Soc. Aug. 4, 2010; 132(30):10521-7.*
Risitano A, Fox KR. Stability of intramolecular DNA quadruplexes: comparison with DNA duplexes. Biochemistry. Jun. 3, 2003;42(21):6507-13.*
Taylor A, Joseph A, Okyere R, Gogichaishvili S, Musier-Forsyth K, Kankia B. Isothermal quadruplex priming amplification for DNA-based diagnostics. Biophys Chem. Jan. 2013;171:1-8.*

(Continued)

*Primary Examiner* — Gary Benzion
*Assistant Examiner* — Olayinka Oyeyemi
(74) *Attorney, Agent, or Firm* — Wood, Herron & Evans, L.L.P.

(57) ABSTRACT

A primer and method for amplification of a target nucleic acid, the primer adapted to conform into a conformation that dissociates from a complementary strand of DNA duplex. The conformation may have a free energy with more favorable thermodynamics than a corresponding DNA duplex, such as a B-DNA duplex. The dissociation may occur during an extension step of an amplification method, such as polymerase chain reaction. The method can proceed isothermally, and the primers may include intrinsic fluorescence.

18 Claims, 16 Drawing Sheets

(56) References Cited

OTHER PUBLICATIONS

Walker GT, Little MC, Nadeau JG, Shank DD. Isothermal in vitro amplification of DNA by a restriction enzyme/DNA polymerase system. Proc Natl Acad Sci U S A.Jan. 1, 1992; 89(1):392-6.*
Pedroso IM, Duarte LF, Yanez G, Burkewitz K, Fletcher TM. Sequence specificity of inter- and ntramolecular G-quadruplex formation by human telomeric DNA. Biopolymers. Sep. 2007; 87(1):74-84.*
Lu M, Guo Q, Kallenbach NR. Thermodynamics of G-tetraplex formation by telomeric DNAs. Biochemistry. Jan. 19, 1993; 32(2):598-601.*
Gray RD, Petraccone L, Buscaglia R, Chaires JB. 2-aminopurine as a probe for quadruplex loop structures. Methods Mol Biol. Jan. 2010; 608:121-36.*
Sun D, Hurley LH. Biochemical techniques for the characterization of G-quadruplex structures: EMSA, DMS footprinting, and DNA polymerase stop assay. Methods Mol Biol. Jan. 2010; 608:65-79.*
Yu HQ, Miyoshi D, Sugimoto N. Characterization of structure and stability of long telomeric DNA G-quadruplexes. J Am Chem Soc. Dec. 6, 2006; 128(48):15461-8.*
Salazar M, Thompson BD, Kerwin SM, Hurley LH. Thermally induced DNA.RNA hybrid to G-quadruplex transitions: possible implications for telomere synthesis by telomerase. Biochemistry. Dec. 17, 1996; 35(50):16110-5.*
Vorlíčková M, Chládková J, Kejnovská I, Fialová M, Kypr J. Guanine tetraplex topology of human telomere DNA is governed by the number of (TTAGGG) repeats. Nucleic Acids Res. Oct. 12, 2005; 33(18):5851-60. Print 2005.*
International Search Report in related PCT/US2012/029880, mailed Oct. 30, 2012, 4 pgs.
Fletcher, T.M. et al., "Effect of DNA secondary structure on human telomerase activity," Biochem., Apr. 21, 1998, vol. 37, No. 16, Abstract only.
Kankia, B.I., "Self-dissociative primers for nucleic acid amplification and detection based on DNA quadruplexes with intrinsic fluorescence," Anal. Biochem., Oct. 12, 2010, vol. 409, No. 1, pp. 59-65.
Gray, R. et al., "Characterization of a K+-Induced Conformational Switch in a Human Telomeric DNA Oligonucleotide Using 2-Aminopurine Fluorescence," Biochem. 2010;49:179-194.
Marchand, C. et al., "Interaction of human nuclear topoisomerase I with guanosine-quartet-forming and guanosine-rich single-stranded DNA and RNA oligonucleotides," J. Biol. Chem. 2001;277(11):8906-8911.
Supplementary European Search Report in corresponding European Patent Application No. 11745310.0, received Jan. 29, 2014, 12 pgs.
Andras, S.C., et al., (2001) Strategies for signal amplification in nucleic acid detection. Molecular biotechnology, 19, 29-44.
Arthanari, H et al, (1998) Fluorescent dyes specific for quadruplex DNA. Nucleic Acids Research, 26:16, 3724-3728.
Becker, A., et al., (1996) A quantitative method of determining initial amounts of DNA by polymerase chain reaction cycle titration using digital imaging and a novel DNA stain. Anal Biochem, 237, 204-207.
Bordelon, H., et al, (2011) Development of a Low-Resource RNA Extraction Cassette Based on Surface Tension Valves, ACS Appl. Mater. Interfaces, 3, 2161-2168.
Borman, S., (2007) Ascent of Quadruplexes—Nucleic acid structures become promising drug targets, Chemical & Engineering News, 85:22, 12-17.
Burge, S., et al., (2006) Survey and Summary: Quadruplex DNA: sequence, topology, and structure, Nucleic Acids Research, 34:19, 5402-5415.
Edwards, K.J., et al., (2009) In Logan, J. et al. (eds.), Performing Real-time PCR. Caister academic Press, Norfolk, UK, pp. 85-93.
Fidalgo Da Silva E., et al., (2002) Using 2-aminopurine fluorescence to measure incorporation of incorrect nucleotides by wild type and mutant bacteriophage T4 DNA polymerases. The Journal of Biological Chemistry, 277, 40640-40649.
Fox, J.D., et al., (2009) In Logan, J. et al. (eds.), Real-Time NASBA. Caister Academic Press, Norfolk, UK, pp. 163-175.
Hardin, C.C., et al., (2001) Thermodynamic and kinetic characterization of the dissociation and assembly of quadruplex nucleic acids. Biopolymers, 56, 147-194.
Hawkins, M.E., (2008) Fluorescent pteridine probes for nucleic acid analysis. Methods of enzymology, 450, 201-231.
Holland, P.M., et al., (1991) Detection of specific polymerase chain reaction product by utilizing the 5'—3' exonuclease activity of Thermus aquaticus DNS polymerase. Proc. Natl. Acad. Sci. USA, 88, 7276-7280.
International Search Report and Written Opinion in International Patent Application No. PCT/US2011/25411, mailed Apr. 29, 2011, 8 pgs.
Jean, J., et al., (2001) 2-Aminopurine fluorescence quenching and lifetimes: Role of base stacking. Proc. Natl. Acad. Sci. USA, 98:1, 37-41.
Jing N., et al., (2001) Structure-activity of inhibition of HIV-1 integrase and virus replication by G-quartet oligonucleotides. DNA Cell Biol., 20, 499-508.
Jing, N., et al., (1998) Structure-activity of tetrad-forming oligonucleotides as a potent anti-HIV therapeutic drug. J. Biol. Chem., 273, 34992-34999.
Jing, N., et al., (1997) Ion selective folding of loop domains in a potent anti-HIV oligonucleotide. Biochemistry, 36, 12498-12505.
Kankia B.I., (2004) Optical absorption assay for strand-exchange reactions in unlabeled nucleic acids. Nucleic Acids Research, 32, 154.
Kankia, B.I., et al., (2001) Folding of the thrombin aptamer into a G-quadruplex with Sr(2+): stability, heat, and hydration. Journal of the American Chemical Society, 123, 10799-10804.
Karimata, H., et al., (2005) Structure and stabiilty of DNA quadruplexes under molecular crowding conditions. Nucleic Acids Symposium, 49, 239-240.
Law, S.M., et al., (1996) Spectroscopic and calorimetric characterizations of DNA duplexes containing 2-aminopurine. Biochemistry, 35, 12329-12337.
Lee, M.A., et al., (2009) In Logan, J. et al. (eds.), Homogeneous Fluorescent Chemistries for Real-time PCR Caister Academic Press, Norfolk, UK pp. 23-45.
Lu, M., et al., (1993) Thermodynamics of G-Tetraplex Formation by Telomeric DNAs. Biochemistry, 32, 598-601.
McLaughlin, L.W., et al., (1988) A new approach to the synthesis of a protected 2-aminopurine derivative and its incorporation into oligodeoxynucleotides containing the Eco RI and Barn HI recognition sites. Nucleic Acids Res., 16, 5631-5644.
Menger, M., et al., (1996) Mg(2+)-dependent conformational changes in the hammerhead ribozyme. Biochemistry, 35, 14710-14716.
Pfaffl, M.W., et al. (2009) In Logan, J. et al. (eds.), Real-time PCR. Caister Academic Press, Norfolk, UK, pp. 65-83.
Rist, M., et al., (2001) Association of an RNA kissing complex analyzed using 2-aminopurine fluorescence. Nucleic Acids Res., 29, 2401-2408.
Smirnov, I., et al., (2000) Effect of loop sequence and size DNA aptamer stability. Biochemistry, 39, 1462-1468.
Stefl, R., et al., (2001) Molecular Dynamics of DNA Quadruplex Molecules Containing Inosine, 6-Thioguanine and 6-Thiopurine. Biophysical Journal, 80, 455-468.
Su, T.-J., et al., (2004) Unusual 2-aminopurine fluorescence from a complex of DNA and the EcoKI methyltransferase. Nucleic Acids Reserch, 32:7, 2223-2230.
Tomita, N., et al., (2008) Loop-mediated isothermal amplification (LAMP) of gene sequences and simple visual detection of products. Nature Protocols, 3, 877-882.
Tyagi,S., et al., (1996) Molecular beacons: probes that fluoresce upon hybridization. Nature Biotechnology, 14, 303-308.
Tyagi, S., et al., (1998) Multicolor molecular beacons for allele discrimination. Nature Biotechnology, 16, 49-53.

(56) References Cited

OTHER PUBLICATIONS

Vincent, M., et al., (2004) Helicase-dependent isothermal DNA amplification. EMBO Reports, 5, 795-800.

Walker, G.T., et al., (1992) Strand displacement amplification—an isothermal, in vitro DNA amplification technique. Nucleic Acids Research, 20, 1691-1696.

Ward, D.C., et al., (1969) Fluorescence studies of nucleotides and polynucleotides. I. Formycin, 2-aminopurine riboside, 2,6-diaminopurine riboside, and their derivatives. J. Biol. Chem., 244, 1228-1237.

Whitcombe, D., et al., (1999) Detection of PCR products using self-probing amplicons and fluorescence. Nat. Biotechnol., 17, 804-807.

Zuker, M., (2003) Mfold web server for nucleic acid folding and hybridization prediction. Nucleic Acids Research, 31, 3406-3415.

Salazar, M., et al., (1996) Thermally Induced DNA-RNA Hybrid to G-Quadruplex Transitions: Possible Implications for Telomere Synthesis by Telomerase, Biochemistry, 35, 16110-16115.

International Search Report and Written Opinion in International Patent Application No. PCT/US2014/021165, mailed Jul. 28, 2014, 13 pgs.

Phan, A.T. et al., "Human telomeric DNA: G-quadruplex, i-motif and Watson-Crick double helix," Nucleic Acids Research (2002) 30(21):4618-4625.

International Preliminary Report on Patentability in International Application No. PCT/US2014/021165, dated Sep. 8, 2015, 11 pgs.

Database Embl [Online] May 29, 1991, "Human Wilms tumor WT1 mRNA for zinc finger protein, Krueppel-like," retrieved from EBI accession No. EM_STD:X51630, Database accession No. X51630.

Summons to Oral Proceedings in European Patent Application No. 11745310.0, mailed Apr. 18, 2016, 13 pgs.

Adams, N.M. et al., "Quadruplex priming amplification for the detection of mRNA from surrogate patient samples," The Royal Society of Chemistry (2014) 9 pgs.

Van Ness, J. et al., "Isothermal reactions for the amplification of oligonucleotides," PNAS (2003) 100(8):4504-4509.

\* cited by examiner

SEQUENCE LISTING

```
<160> NUMBER OF SEQ ID NOS: 24

<210> SEQ ID NO 1
<211> LENGTH: 16
<212> TYPE: DNA
<213> ORGANISM: Artificial Sequence
<220> FEATURE:
<223> OTHER INFORMATION: Primers

<400> SEQUENCE: 1
gggtgggtgg gtgggt                                                     16

<210> SEQ ID NO 2
<211> LENGTH: 15
<212> TYPE: DNA
<213> ORGANISM: Artificial Sequence
<220> FEATURE:
<223> OTHER INFORMATION: Primers

<400> SEQUENCE: 2
gggtgggtgg gtggg                                                      15
```

-continued

```
<210> SEQ ID NO 3
<211> LENGTH: 15
<212> TYPE: DNA
<213> ORGANISM: Artificial Sequence
<220> FEATURE:
<223> OTHER INFORMATION: Primers

<400> SEQUENCE: 3
cccacccacc ctccc                                                     15

<210> SEQ ID NO 4
<211> LENGTH: 17
<212> TYPE: DNA
<213> ORGANISM: Artificial Sequence
<220> FEATURE:
<223> OTHER INFORMATION: Primers

<400> SEQUENCE: 4
gtaaaacgac ggccagt                                                   17

<210> SEQ ID NO 5
<211> LENGTH: 17
<212> TYPE: DNA
<213> ORGANISM: Artificial Sequence
<220> FEATURE:
<223> OTHER INFORMATION: Primers

<400> SEQUENCE: 5
ggaaacagct atgacca                                                   17

<210> SEQ ID NO 6
<211> LENGTH: 17
<212> TYPE: DNA
<213> ORGANISM: Artificial Sequence
<220> FEATURE:
<223> OTHER INFORMATION: Primers

<400> SEQUENCE: 6
caggaaacag ctatgac                                                   17

<210> SEQ ID NO 7
<211> LENGTH: 19
<212> TYPE: DNA
<213> ORGANISM: Artificial Sequence
<220> FEATURE:
<223> OTHER INFORMATION: Primers

<400> SEQUENCE: 7
cggcgggagg gtgggtggg                                                 19

<210> SEQ ID NO 8
<211> LENGTH: 19
<212> TYPE: DNA
<213> ORGANISM: Artificial Sequence
<220> FEATURE:
<223> OTHER INFORMATION: Primers

<400> SEQUENCE: 8
cccacccacc ctcccgccg                                                 19

<210> SEQ ID NO 9
<211> LENGTH: 16
<212> TYPE: DNA
<213> ORGANISM: Artificial Sequence
<220> FEATURE:
<223> OTHER INFORMATION: Primers
```

```
<400> SEQUENCE: 9
gggtgggtgg gtgggt                                              16

<210> SEQ ID NO 10
<211> LENGTH: 15
<212> TYPE: DNA
<213> ORGANISM: Artificial Sequence
<220> FEATURE:
<223> OTHER INFORMATION: Primers
<220> FEATURE:
<221> NAME/KEY: misc_feature
<223> OTHER INFORMATION: 2Ap
<220> FEATURE:
<221> NAME/KEY: misc_feature
<222> LOCATION: (4)..(4)
<223> OTHER INFORMATION: 2Ap

<400> SEQUENCE: 10
gggngggtgg gtggg                                               15

<210> SEQ ID NO 11
<211> LENGTH: 14
<212> TYPE: DNA
<213> ORGANISM: Artificial Sequence
<220> FEATURE:
<223> OTHER INFORMATION: Primers
<220> FEATURE:
<221> NAME/KEY: misc_feature
<223> OTHER INFORMATION: 2Ap
<220> FEATURE:
<221> NAME/KEY: misc_feature
<222> LOCATION: (4)..(4)
<223> OTHER INFORMATION: 2Ap

<400> SEQUENCE: 11
gggngggtgg gtgg                                                14

<210> SEQ ID NO 12
<211> LENGTH: 13
<212> TYPE: DNA
<213> ORGANISM: Artificial Sequence
<220> FEATURE:
<223> OTHER INFORMATION: Primers
<220> FEATURE:
<221> NAME/KEY: misc_feature
<222> LOCATION: (4)..(4)
<223> OTHER INFORMATION: 2Ap

<400> SEQUENCE: 12
gggngggtgg gtg                                                 13

<210> SEQ ID NO 13
<211> LENGTH: 13
<212> TYPE: DNA
<213> ORGANISM: Artificial Sequence
<220> FEATURE:
<223> OTHER INFORMATION: Primers
<220> FEATURE:
<221> NAME/KEY: misc_feature
<222> LOCATION: (4)..(4)
<223> OTHER INFORMATION: 2Ap

<400> SEQUENCE: 13
gggngggtgg gtg                                                 13

<210> SEQ ID NO 14
<211> LENGTH: 51
<212> TYPE: DNA
<213> ORGANISM: Artificial Sequence
```

```
<220> FEATURE:
<223> OTHER INFORMATION: Primers

<400> SEQUENCE: 14
gggagggtgg gtgggcctct ttggttcggc agttatccca cccaccctcc c          51

<210> SEQ ID NO 15
<211> LENGTH: 17
<212> TYPE: DNA
<213> ORGANISM: Artificial Sequence
<220> FEATURE:
<223> OTHER INFORMATION: Primers

<400> SEQUENCE: 15
gggcgggagg gtgggtg                                                17

<210> SEQ ID NO 16
<211> LENGTH: 59
<212> TYPE: DNA
<213> ORGANISM: Artificial Sequence
<220> FEATURE:
<223> OTHER INFORMATION: Primers

<400> SEQUENCE: 16
gcgcccctcc cacccaccct attgacggct tggtttctcc gggtgggtgg gagggcgcg  59

<210> SEQ ID NO 17
<211> LENGTH: 58
<212> TYPE: DNA
<213> ORGANISM: Artificial Sequence
<220> FEATURE:
<223> OTHER INFORMATION: Primers

<400> SEQUENCE: 17
gcgccctccc acccacccta ttgacggctt ggtttctccg cgtgcgtgct agccgcgc   58

<210> SEQ ID NO 18
<211> LENGTH: 59
<212> TYPE: DNA
<213> ORGANISM: Artificial Sequence
<220> FEATURE:
<223> OTHER INFORMATION: Primers

<400> SEQUENCE: 18
gcgcgggagg gtgggtgggc ctctttggtt cggcagttat cccacccacc ctcccgcgc  59

<210> SEQ ID NO 19
<211> LENGTH: 17
<212> TYPE: DNA
<213> ORGANISM: Artificial Sequence
<220> FEATURE:
<223> OTHER INFORMATION: Primers
<220> FEATURE:
<221> NAME/KEY: misc_feature
<222> LOCATION: (3)..(3)
<223> OTHER INFORMATION: 2Ap
<220> FEATURE:
<221> NAME/KEY: misc_feature
<222> LOCATION: (8)..(8)
<223> OTHER INFORMATION: 2Ap

<400> SEQUENCE: 19
gcgcgggngg gtgggtg                                                17

<210> SEQ ID NO 20
<211> LENGTH: 15
<212> TYPE: DNA
```

```
<213> ORGANISM: Artificial Sequence
<220> FEATURE:
<223> OTHER INFORMATION: Primers
<220> FEATURE:
<221> NAME/KEY: misc_feature
<222> LOCATION: (7)..(7)
<223> OTHER INFORMATION: 2Ap

<400> SEQUENCE: 20
ggttggngtg gttgg                                                    15

<210> SEQ ID NO 21
<211> LENGTH: 15
<212> TYPE: DNA
<213> ORGANISM: Artificial Sequence
<220> FEATURE:
<223> OTHER INFORMATION: Primers
<220> FEATURE:
<221> NAME/KEY: misc_feature
<222> LOCATION: (4)..(4)
<223> OTHER INFORMATION: 6MI

<400> SEQUENCE: 21
gggngggcgg gcggg                                                    15

<210> SEQ ID NO 22
<211> LENGTH: 19
<212> TYPE: DNA
<213> ORGANISM: Artificial Sequence
<220> FEATURE:
<223> OTHER INFORMATION: Primers

<400> SEQUENCE: 22
gcgcgggtgg gtgggtggg                                                19

<210> SEQ ID NO 23
<211> LENGTH: 17
<212> TYPE: DNA
<213> ORGANISM: Artificial Sequence
<220> FEATURE:
<223> OTHER INFORMATION: Primers
<220> FEATURE:
<221> NAME/KEY: misc_feature
<222> LOCATION: (8)..(8)
<223> OTHER INFORMATION: 2Ap

<400> SEQUENCE: 23
cggcgggngg gtgggtg                                                  17

<210> SEQ ID NO 24
<211> LENGTH: 15
<212> TYPE: DNA
<213> ORGANISM: Artificial Sequence
<220> FEATURE:
<223> OTHER INFORMATION: Primers
<220> FEATURE:
<221> NAME/KEY: misc_feature
<222> LOCATION: (3)..(3)
<223> OTHER INFORMATION: 2Ap

<400> SEQUENCE: 24
ggntggtgtg gttgg                                                    15
```

PRIMERS AND METHODS FOR NUCLEIC ACID AMPLIFICATION

CROSS-REFERENCE TO RELATED APPLICATION

This application is a U.S. national phase filing under 35 U.S.C. §371 of International Patent Application No. PCT/US2011/025411, filed Feb. 18, 2011, entitled "Primers and Methods for Nucleic Acid Amplification," which claims priority to and the benefit of the filing date of U.S. Provisional Patent Application Ser. No. 61/338,475, entitled "Quadruplex Priming for Polymerase Chain Reaction," filed on Feb. 19, 2010, the disclosures of which are hereby incorporated by reference herein in their entireties.

FIELD OF THE INVENTION

The present invention relates generally to the polymerase chain reaction (PCR), and more specifically to novel primers used in PCR and a novel method for amplification of a target sequence in PCR.

BACKGROUND

This section is intended to introduce the reader to various aspects of art that may be related to various aspects of the present invention, which are described and/or claimed below. This discussion is believed to be helpful in providing the reader with background information to facilitate a better understanding of various aspects of the present invention. Accordingly, it should be understood that these statements are to be read in this light, and not as admissions of prior art.

Since its initial design by Kary Mullis in 1984, the polymerase chain reaction (PCR) has impacted nearly every field in molecular biology, genetics, and forensic science. PCR is a technique to amplify a single or few copies of a particular nucleic acid sequence, e.g., DNA (the target DNA sequence), across several orders of magnitude, thereby generating thousands to millions of copies of the sequence. PCR is the main tool presently used to amplify nucleic acid and study gene expression.

PCR relies on "thermal cycling," which includes cycles of repeated heating and cooling of the DNA and other reaction components to cause DNA denaturation (i.e., separation of the double-stranded DNA into its sense and antisense strands) followed by enzymatic replication of the DNA. The other reaction components include short oligonucleotide DNA fragments known as "primers," which contain sequences complementary to at least a portion of the target DNA sequence, and a DNA polymerase. These are components that facilitate selective and repeated amplification of the target sequence. As PCR progresses, the DNA generated is itself used as a template for further replication in subsequent cycles, creating a chain reaction in which the target DNA sequence is exponentially amplified.

More specifically, the DNA polymerase used in PCR is thermostable (and thus avoids enzyme denaturation at high temperatures) and amplifies target DNA by in vitro enzymatic replication. One such thermostable DNA polymerase is Taq polymerase, an enzyme originally isolated from the bacterium *Thermus aquaticus*. The DNA polymerase enzymatically assembles a new DNA strand from deoxynucleoside triphosphates (dNTPs) by using the denatured single-stranded DNA as a template. As is known to those of ordinary skill in the art, a deoxynucleoside triphosphate is deoxyribose) having three phosphate groups attached, and having one base (adenine, guanine, cytosine, thymine) attached. However, as used herein, it will be recognized by those of ordinary skill in the art that arsenic may be substituted for phosphorous in the triphosphate back bone any dNTP. The initiation of DNA synthesis and the selectivity of PCR results from the use of primers that are complementary to the DNA region targeted for amplification under specific thermal cycling conditions.

Thus, a basic PCR set up includes multiple components. These include: (1) a DNA template that contains the target DNA region to be amplified; (2) primers that are complementary to the 3' ends of each of the sense strand and anti-sense strand of the target DNA; (3) a thermostable DNA polymerase such as Taq polymerase; and (4) dNTPs, the building blocks from which the DNA polymerases synthesizes a new DNA strand. Additionally, the reaction will generally include other components such as a buffer solution providing a suitable chemical environment for optimum activity and stability of the DNA polymerase, divalent cations (generally magnesium ions), and monovalent cation potassium ions ($K^+$).

PCR is commonly carried out in a reaction volume of 10-200 μl in small reaction tubes (0.2-0.5 ml volumes) in an apparatus referred to as a thermal cycler. The thermal cycler heats and cools the reaction tubes to achieve the temperatures required at each of the following steps of the reaction:

Denaturation Step:

This step consists of heating the reaction to usually around 94-98° C. for approximately 20-30 seconds. It causes denaturation of the DNA template by disrupting the hydrogen bonds between complementary bases, yielding single strands of DNA.

Annealing Step:

The reaction temperature is lowered to usually around 50-65° C. for approximately 20-40 seconds allowing annealing of the primers to the single-stranded DNA template. Stable DNA-DNA hydrogen bonds are formed when the primer sequence closely matches the template sequence. The polymerase (e.g., Taq polymerase) binds to the primer-template hybrid and begins DNA synthesis.

Extension Step:

The temperature at this step depends on the DNA polymerase used. Taq polymerase has its optimum activity temperature at about 75° C., and commonly a temperature of 72° C. is used with this enzyme. At this step the DNA polymerase synthesizes a new DNA strand complementary to the DNA template strand by adding dNTPs that are complementary to the template in the 5' to 3' direction, condensing the 5'-phosphate group of the dNTPs with the 3'-hydroxyl group at the end of the extending DNA strand. The extension time depends on the DNA polymerase used and on the length of the DNA fragment to be amplified. Under optimum conditions, at each extension step the amount of the target DNA is doubled, leading to exponential amplification of the specific target DNA.

PCR usually includes of a series of 20 to 40 repeated cycles of the above-described denaturation, annealing, and extension steps. The cycling is often preceded by a single initialization step at a high temperature (>90° C.), and followed by one final hold at the end for final product extension or brief storage. The initialization step consists of heating the reaction to a temperature of usually 94-96° C. (or 98° C. if extremely thermostable polymerases are used), which is held for 1-9 minutes. The final hold usually occurs at 4-15° C. for an indefinite time and may be employed for short-term storage of the reaction. The temperatures used and the length of time they are applied in each cycle depend on a variety of parameters. These include the enzyme used for DNA synthesis, the concentration of divalent ions and dNTPs in the reaction, and the melting temperature ($T_m$) of the primers.

Following thermal cycling, agarose gel electrophoresis may be employed for size separation of the PCR products to check whether PCR amplified the target DNA fragment. The size(s) of the PCR products is determined by comparison with a molecular weight marker, which contains DNA fragments of known size, run on the gel alongside the PCR products.

There are many applications of PCR. For example, real-time PCR (RT-PCR) is an established tool for DNA quantification that measures the accumulation of DNA product after each round of PCR amplification. Thus, RT-PCR enables both detection and quantification of one or more specific sequences in a DNA sample (as absolute number of copies or relative amount when normalized to DNA input or additional normalizing genes). Such quantitative PCR methods allow the estimation of the amount of a given sequence present in a sample—a technique often applied to quantitatively determine levels of gene expression.

RT-PCR procedure follows the general principle of PCR. However, in RT-PCR, the amplified DNA is detected as the reaction progresses in real time (whereas in standard PCR, the product of the reaction is detected at the end of the reaction). One common method for detection of products in RT-PCR is the use of nonspecific fluorescent dyes that intercalate with double-stranded DNA (dsDNA). For example, SYBR Green is an asymmetrical cyanine dye that binds to dsDNA, and the resulting DNA-dye complex absorbs blue light ($\lambda_{max}$=488 nm) and emits green light ($\lambda_{max}$=522 nm). The DNA-binding dye, such as SYBR Green, binds to all dsDNA in PCR, causing fluorescence of the dye. An increase in DNA product during PCR therefore leads to an increase in fluorescence intensity and is measured at each cycle, thus allowing DNA concentrations to be quantified.

Another method for detection of products in RT-PCR is the use of sequence-specific DNA probes, which are oligonucleotides that are labeled with a fluorescent reporter that permits detection after hybridization of the probe with its complementary DNA target. Many of these probes include a DNA-based probe having a fluorescent reporter (e.g., at one end of the probe) and a quencher of fluorescence (e.g., at the opposite end of the probe). The close proximity of the reporter to the quencher prevents detection of its fluorescence; breakdown of the probe by the 5' to 3' exonuclease activity of the Taq polymerase breaks the reporter-quencher proximity and thus allows unquenched emission of fluorescence, which can be detected. An increase in the product targeted by the reporter probe at each PCR cycle therefore causes a proportional increase in fluorescence due to the breakdown of the probe and release of the reporter. Examples of such probes well known to those of ordinary skill in the art are molecular beacon probes, TagMan® probes, and Scorpion™ probes.

Molecular beacons are single-stranded oligonucleotide probes that form a hairpin-shaped stem-loop structure. The loop contains a probe sequence that is complementary to a target sequence in the PCR product. The stem is formed by the annealing of complementary sequences that are located on either side of the probe sequence. A fluorophore and quencher are covalently linked to the ends of the hairpin. Upon hybridization to a target sequence the fluorophore is separated from the quencher and fluorescence increases. Hybridization usually occurs after unfolding of the hairpin and product duplexes in the denaturation step of the next PCR cycle.

TaqMan® probes are single-stranded unstructured oligonucleotides. They have a fluorophore attached to the 5' end and a quencher attached to the 3' end. When the probes are free in solution, or hybridized to a target, the proximity of the fluorophore and quencher molecules quenches the fluorescence. During PCR, when the polymerase replicates a template on which a TagMan® probe is bound, the 5'-nuclease activity of the polymerase cleaves the probe. Upon cleavage, the fluorophore is released and fluorescence increases.

Scorpion™ probes use a single oligonucleotide that consists of a hybridization probe (stem-loop structure similar to molecular beacons) and a primer linked together via a non-amplifiable monomer. The hairpin loop contains a specific sequence that is complementary to the extension product of the primer. After extension of the primer during the extension step of a PCR cycle, the specific probe sequence is able to hybridize to its complement within the extended portion when the complementary strands are separated during the denaturation step of the subsequent PCR cycle, and fluorescence will thus be increased (in the same manner as molecular beacons).

However, there are drawbacks to the probes used to detect products in RT-PCR. For example, in the case of the use of nonspecific fluorescent dyes, dsDNA dyes such as SYBR Green will bind to all dsDNA PCR products, including nonspecific PCR products (such as "primer dimers"—i.e., primer molecules that have hybridized to each other). This interferes with and prevents accurate quantification of the intended target DNA sequence.

The use of sequence-specific DNA probes (e.g., molecular beacons, TagMan®, and Scorpion™ probes) reduces or eliminates some of the drawbacks inherent in nonspecific fluorescent dyes. For example, fluorescent reporter probes detect only the DNA containing the probe sequence; therefore, use of the reporter probe significantly increases specificity, and enables quantification even in the presence of non-specific DNA amplification. Fluorescent probes can be used in multiplex assays—for detection of several genes in the same reaction—based on specific probes with different-colored labels, provided that all targeted genes are amplified with similar efficiency. The specificity of fluorescent reporter probes also prevents interference of measurements caused by primer dimers.

However, there are also drawbacks with these sequence-specific probes. For example, there are several disadvantages with molecular beacons. First, they require two bulky and costly tags (fluorophore and quencher). Second, the assay requires a separate probe for each template (i.e. mRNA), which dramatically increases the design effort and expense. Third, the mechanism uses separate binding sites for primer and probe sequences, which introduces another component (probe oligonucleotide) to an already complex reaction, and adds additional design limitations due to the need to avoid interactions between the probe and primers. Fourth, hybridization of the probe requires heating steps to unfold the product duplex and hairpin. Consequently, molecular beacons can't be used under isothermal conditions. Fifth, design of the probe requires considerable effort and knowledge of nucleic acid thermodynamics. And sixth, probe hybridization involves a bimolecular probe-primer system. This makes the reaction entropically unfavorable, slows down hybridization, and complicates product detection at exponential growth. The hybridization is much faster and efficient with a monomolecular probe-primer system [as described in Whitcombe, D. et al. (1999) Detection of PCR products using self-probing amplicons and fluorescence. *Nat Biotechnol*, 17, 804-807, incorporated by reference herein in its entirety].

All of the shortcomings listed above for molecular beacons hold true for TaqMan® probes. And, an additional disadvantage of TaqMan® probes is that they require the 5'-nuclease activity of the DNA polymerase used for PCR.

Additionally, many of the shortcomings listed for molecular beacons hold true for Scorpion™ probes. First, they require two bulky and costly tags (fluorophore and quencher). Second, the assay requires a separate probe for each template (i.e. mRNA), which dramatically increases the design effort and expense. Third, the mechanism uses separate binding sites for primer and probe sequences, which introduces another component (probe oligonucleotide) to an already complex reaction, and adds additional design limitations due to the need to avoid interactions between the probe and primers. Fourth, hybridization of the probe requires heating steps to unfold the product duplex and hairpin. Consequently, molecular beacons can't be used under isothermal conditions. And fifth, design of the probes requires considerable effort and knowledge of nucleic acid thermodynamics.

Further, fluorescent reporter probes do not prevent the inhibitory effect of the primer dimers, which may depress accumulation of the desired products in the reaction.

Apart from any problems with probes listed above, there are further problems inherent in PCR and RT-PCR. For example, one of the most important factors limiting the yield of specific product is the competition between primer binding and self-annealing of the product. At the initial stage of PCR, product molecules are at low enough concentrations that product self-annealing does not compete with primer binding and amplification proceeds at an exponential rate. However, with accumulation of product DNA, self-annealing becomes dominant and PCR slows down and eventually DNA amplification ceases.

Temperature cycling is another limitation of PCR since it requires expensive instrumentation for thermocycling and complicates rapid detection of pathogens in the field and at point-of-care. In addition, rapid temperature changes facilitate product mis-priming and affect stability of the polymerases.

To decrease certain of the above-described drawbacks, such as the cost of probe synthesis, several attempts have been made to use intrinsic fluorescence of nucleotides. For example, 2-aminopurine (2Ap) has been used as a label for the detection of product in RT-PCR. 2Ap is a fluorescent analog of adenosine and has been used as a site-specific probe of nucleic acid structure and dynamics because it base pairs with cytosine in a wobble configuration or with thymine in a Watson-Crick geometry. 2Ap has been incorporated into stem-loop probes [as described in Walker, G. T. et al. (1992) Strand displacement amplification—an isothermal, in vitro DNA amplification technique. *Nucleic acids research*, 20, 1691-1696]. Upon hybridization to a target sequence, a several-fold increase in fluorescence was observed due to the change of 2Ap from a double-helix (quenched state) to a single-stranded region (emitted state). However, the sensitivity of the 2Ap probes is insufficient for accurate monitoring of PCR, since 2Ap is still significantly quenched in single strands.

SUMMARY OF THE INVENTION

Certain exemplary aspects of the invention are set forth below. It should be understood that these aspects are presented merely to provide the reader with a brief summary of certain forms the invention might take and that these aspects are not intended to limit the scope of the invention. Indeed, the invention may encompass a variety of aspects that may not be explicitly set forth below.

In an overarching aspect, the present invention provides a new amplification system that reduces or eliminates the shortcomings of PCR and RT-PCR described above. For example, as described above, PCR is limited by competition between primer binding and undesired self-annealing of target DNA. One aspect of the present invention inhibits self-annealing by providing at least one primer, such as an oligonucleotide primer, for amplification of a target nucleic acid (e.g., DNA), wherein the primer is adapted to conform into a structure that can dissociate from a DNA duplex structure in the absence of heating. In other words, the primer includes a sequence that naturally conforms into a structure, such as a quadruplex structure (or any other non-B DNA configuration or other DNA structure) in which intramolecular base pairing allows or causes the primer to dissociate from the double stranded DNA—of which it is one strand—and form its particular structure. This structure may be referred to herein as a "dissociative structure" or "dissociative conformation" or the like. This example of such a primer may conform into the structure such as during the extension step of PCR. As this occurs, the primer necessarily separates from its binding site on the target DNA sequence while the extending portion (DNA polymerase adding dNTPs to the sequence) remains bound (at least temporarily) in a double-stranded configuration. In other words, one aspect of the invention is that the primer can be of any sequence wherein its free energy can drive PCR upon extension of the primer or upon interaction with a polymerase during PCR.

Further, the primers used in this aspect of the present invention may be universal. In other words, each primer in the primers used in the reaction includes the same sequence (or a substantially similar sequence that allows amplification to occur). As is known to those of ordinary skill in the art, in standard PCR at least two different primers (i.e., having two different sequences) are used (i.e., a first set of primers, wherein each primer of the first set includes the same or similar sequence, and a second set of primers wherein each primer of the second set includes the same or similar sequence, that sequence being different from the sequence of the primers in the first set). The need for the two sets of primers is to provide for amplification using each of the single strands from the DNA. Thus, one strand will be replicated using primers from the first set. The second strand (which is complementary to the first strand) will also be replicated. However, as that second strand is complementary to the first strand, the primers of the second set may be complementary to the primers of the first set. This creates the problem of primer-dimers (when the primers hybridize to one another—rather than to the target template denatured DNA strands). However, in the present invention, each of the primers used have the same or similar sequence. There is no second set of complementary primers that is needed (as will be described in greater detail below). As such, there are no other complementary primers for the primers of the present application to hybridize to, thus eliminating the problem of primer dimers. Further, as the end being extended is currently bound with the target region, self-annealing of product is eliminated. And, the original primer binding site on the target DNA region is open for binding of another primer.

While "at least one primer" and a site being "open for binding of another primer" are discussed herein, it will be recognized by those of ordinary skill in the art that the "at least one primer" and the "another primer" may have the same sequence (or substantially similar sequence) as it is known that PCR employs multiple copies of a primer for amplification of a target DNA sequence. Further, as is known to those of ordinary skill in the art, the reaction components generally include multiple copies of primers. Thus, it will be understood that "at least one primer" or "one primer" or "a primer" or "the primer" or like references may refer to a single primer, or a primer among a set of multiple copies of the same or similar primers. Further, while various PCR procedures described herein are discussed as amplifying DNA, those of ordinary skill in the art will recognize that does not limit the disclosure to those seeking DNA sequences, as procedures such as reverse transcription PCR are well known, wherein reverse transcriptase reverse transcribes RNA into cDNA, which is then amplified by PCR.

In one aspect, the primer(s) may be based on any sequence that is capable of forming a quadruplex structure (or other structure that allows or causes the primer to dissociate from a double-stranded DNA and form the particular structure—e.g., a quadruplex—such as during an extension step of PCR). As is known to those of ordinary skill in the art, due to their base pairing properties, nucleic acid sequences can often form specific structures under certain solution conditions. For example, in the presence of certain metal ions (e.g., $K^+$), short guanine (G)-rich sequences fold into a structure known as a G-quartet or quadruplex. Quadruplexes are very stable and biophysical studies have shown that they possess intrinsic optical properties (e.g., absorb light at 300 nm) that distinguish them from other secondary structures. Previously, quadruplex-formation assays have been developed that exploit this unique quadruplex signature to study enzymes that cleave DNA [Kankia, B. I. (2006) *A real-time assay for monitoring nucleic acid cleavage by quadruplex formation*, Nucleic acids research, 34, p. 141] or facilitate strand-exchange reactions [Kankia, B. I. (2004) *Optical absorption assay for strand-exchange reactions in unlabeled nucleic acids*, Nucleic acids research, 32, p. 154]. Briefly, when G-rich sequences with the potential to form a quadruplex are incorporated into DNA substrates they are initially in the quenched state. Upon enzymatic activity (i.e., strand cleavage or strand-exchange) the released sequence folds into a quadruplex and becomes visible when monitored by absorption or fluorescence spectroscopy.

One aspect of the present invention, then, uses the free energy of DNA quadruplexes (or other non-quadruplex conformations) to drive unfavorable (endergonic) reactions of nucleic acids (e.g., isothermal PCR). The key point of such reactions is that some sequences—e.g., some G-rich sequences—are capable of forming quadruplexes (or other conformations) with significantly more favorable thermodynamics than the corresponding DNA duplexes. The sequences are incorporated within DNA duplexes, which after interaction with an initiator (e.g., DNA polymerase) self-dissociate from the complementary strand and fold into quadruplexes (or other conformations). The energy of formation of the non B-DNA structure, or other DNA structure is used to drive PCR at substantially constant temperature.

Another aspect of the present invention then provides a primer or primers having sequences that are capable of forming structures to dissociate from a DNA duplex, such as a quadruplex. Thus, in certain embodiments, the primer may include a sequence that is generally based on a sequence in the form of $d(G_{3+}N_{1-7}G_{3+}N_{1-7}G_{3+}N_{1-7}G_3)$. In certain embodiments, the sequence may be a G-rich sequence. And, in one particular embodiment, the primer(s) may be based on the sequence GGGTGGGTGGGTGGGT [SEQ. ID. NO. 1] ["$(GGGT)_4$"], which is capable of forming a very stable quadruplex, even in the presence of a complementary strand. By being "based on" the sequence $(GGGT)_4$ [SEQ. ID. NO. 1], those of ordinary skill in the art will recognize that substitutions and/or deletions may be made to this base sequence, so long as the resulting primer based on the $(GGGT)_4$ [SEQ. ID. NO. 1] sequence remains able to conform into a quadruplex structure, either on its own or during an extension step of a PCR process. The particular primers may be shorter sequences based on the $(GGGT)_4$ [SEQ. ID. NO. 1] sequence. These primers thus may be unable to fold into a quadruplex on their own, but will fold into a quadruplex structure after polymerase elongation and dissociation from the target site, and will stay folded at annealing of the next cycle. This process is referred to herein as "quadruplex priming amplification" (QPA). Because QPA inhibits product self-annealing and increases the number of PCR cycles within the exponential growth phase, this aspect of the present invention improves efficiency of PCR by elongating the window of exponential amplification. While a particular sequence capable of forming such a quadruplex structure—e.g., $(GGGT)_4$ [SEQ. ID. NO. 1]—is described in this embodiment (and while this process is referred to as "Quadruplex Priming Amplification" or "QPA"), it will be recognized by those of ordinary skill in the art that the invention is not limited to the particular sequence, or to a sequence that forms a quadruplex, and that any sequence that dissociates from a DNA duplex to form another structure (whether quadruplex or a structure other than a quadruplex) may be used in accordance with the principles of the present invention.

Further, since the exemplary quadruplex structure is more stable than its corresponding duplex, unfolding of the duplex or release of target for the coming primers can occur without the need of substantial temperature change or any temperature change. In other words, in standard PCR, following the extension step, the DNA is in a duplex form. The next cycle then begins by raising the temperature to a point that the double-stranded DNA again denatures (i.e., separates into single strands). This is necessary in order to provide the separated sense and anti-sense DNA strands for primer binding (to each of the strands), followed by elongation during the next extension step (once the temperature of the reaction is reduced). However, by using primers based on the $(GGGT)_4$ [SEQ. ID. NO. 1] sequence, the primers and extending nucleotides that are added during the extension step naturally conform into the quadruplex structure. As this occurs, the primer (forming the quadruplex structure) naturally separates from the target DNA sequence complementary to the primer, thereby leaving the target region complementary to the primer exposed in single-stranded form for binding of the next primer. This occurs without requiring raising of the temperature to denature the strands from one another. Thus, QPA can proceed under isothermal conditions. And so, the isothermal DNA amplification provided by the present invention does not require expensive instrumentation for thermocycling and allows DNA amplification in the field and at point-of-care.

Thus, another aspect of the present invention provides an isothermic process for amplifying at least one target nucleic acid sequence contained in a nucleic acid or a mixture of nucleic acids. The process includes treating a nucleic acid or a mixture of nucleic acids with at least one oligonucleotide primer adapted to conform into a quadruplex structure during an extension step of a polymerase chain reaction, under isothermic conditions. During this isothermic process, for the at least one nucleic acid sequence being amplified, an extension product of the at least one oligonucleotide primer is synthesized which is complementary to a strand from the nucleic acid or mixture of nucleic acids. In this process, the at least one oligonucleotide primer is selected so as to be sufficiently complementary to the strand from the nucleic acid or a mixture of nucleic acids to hybridize therewith such that the extension product synthesized from the at least one oligonucleotide primer, when it is separated from its complement, can serve as a template for further synthesis of an extension product of another oligonucleotide primer.

Further, as described above, a drawback of current RT-PCR-specific quantification systems is that they use FRET-based applications (Förster Resonance Energy Transfer), which require costly synthesis and considerable effort to design a sensitive probe. A quantification mechanism that uses intrinsic fluorescence of primers will significantly simplify the detection process. Thus, another aspect of the present invention includes a quadruplex forming primer having a sequence with incorporated 2Ap, which emits strong fluorescence upon quadruplex formation. In one particular embodiment, the 2Ap can be incorporated into a primer based on the (GGGT)4 [SEQ. ID. NO. 1] sequence as follows: GGG(2Ap)GGGTGGGTGGG (referred to herein as "2Ap-G3T") [SEQ. ID. NO. 10]. Thus, another aspect of the present invention provides a QPA-based real-time quantification system (RT-QPA) using 2Ap as a sensitive probe for quantification.

Thus, this aspect of the present invention provides a real-time quantification PCR method for detecting amplification of a target nucleic acid. The method includes treating a nucleic acid or a mixture of nucleic acids with at least one oligonucleotide primer adapted to conform into a quadruplex structure (or other dissociative structure) during an extension step of a polymerase chain reaction, under conditions such that for the at least one nucleic acid sequence being amplified an extension product of the at least one oligonucleotide primer is synthesized which is complementary to a strand from the nucleic acid or a mixture of nucleic acids. In the method, the at least one oligonucleotide primer includes a label that is quenched when the at least one oligonucleotide primer is in a non-quadruplex conformation and that is detectable when the at least one oligonucleotide primer is in a quadruplex conformation.

Thus, for example, after polymerase elongation in RT-QPA, specifically designed guanine-rich primer(s) are capable of forming quadruplexes with significantly more favorable thermodynamics than the corresponding DNA duplexes. As a result, target sequences are always accessible for the primers since their complementary strands are trapped in a quadruplex conformation and DNA amplification can proceed under isothermal conditions. In addition, 2Ap nucleotides incorporated and fully quenched within the primers regain maximum emission upon quadruplex formation allowing very simple and accurate detection of product DNA. Thus, the quadruplex priming amplification (QPA) (i) lacks a product self-annealing; (ii) can proceed under isothermal conditions; and (iii) uses intrinsic fluorescence of primers for quantification of DNA products.

BRIEF DESCRIPTION OF THE DRAWINGS

The accompanying drawings, which are incorporated in and constitute a part of this specification, illustrate embodiments of the invention and, together with the general description of the invention given above and the detailed description of the embodiments given below, serve to explain the principles of the present invention.

DETAILED DESCRIPTION

One or more specific embodiments of the present invention will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Figure 1:
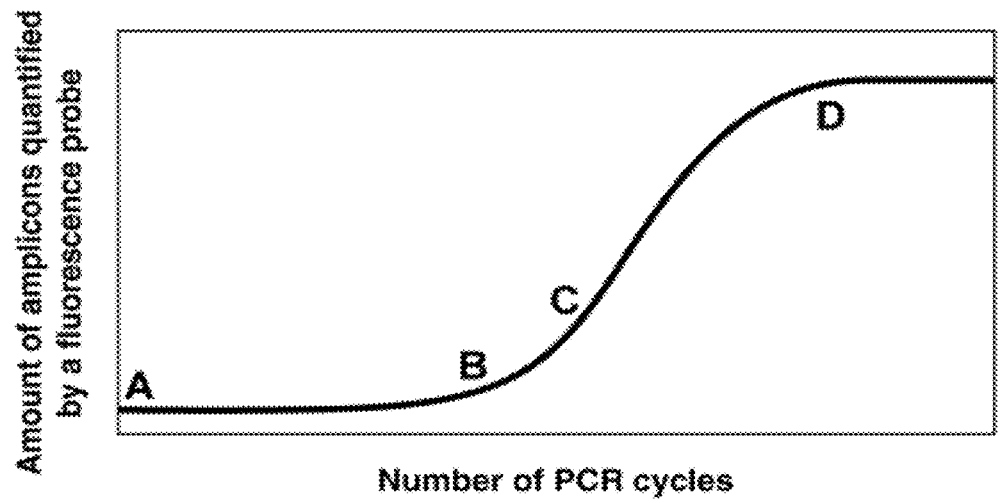
FIG. 1 is a graph showing a typical RT-PCR curve.

As described above, in an overarching aspect, the present invention provides a new amplification system that reduces or eliminates the shortcomings of PCR described above. For example, as described above, PCR is limited by competition between primer binding and undesired self-annealing of target DNA. Referring to FIG. 1, which shows a typical PCR, at the initial stage of PCR, product molecules are at low enough concentrations that product self-annealing does not compete with primer binding and amplification proceeds at an exponential rate (see the AC segment, FIG. 1; the AB segment corresponds to exponential phase undetectable by fluorescence measurements). However, with accumulation of product DNA, self-annealing becomes dominant and PCR slows (CD segment, FIG. 1) and eventually DNA amplification ceases (plateau, FIG. 1).

One aspect of the present invention inhibits this self-annealing by providing at least one primer, such as an oligonucleotide primer, for amplification of a target nucleic acid (e.g., DNA), wherein the primer is adapted to conform into a structure that can dissociate from a DNA duplex structure in the absence of heating. In other words, the primer includes a sequence that naturally conforms into a structure, such as a quadruplex structure (or any other non-B DNA configuration or other DNA structure) in which intramolecular base pairing allows or causes the primer to dissociate from the double stranded DNA—of which it is one strand—and form its particular structure. This structure may be referred to herein as a "dissociative structure" or "dissociative conformation" or the like. As one non-limiting example, the primer may be adapted to conform into a quadruplex structure. The primer may conform into the quadruplex structure during an extension step of PCR. As this occurs, the primer necessarily separates form its binding site on the target DNA sequence while the extending portion (DNA polymerase adding dNTPs to the sequence) remains bound (at least temporarily) in a double-stranded configuration. Again, it will be recognized by those of skill in the art that quadruplex structures are merely exemplary, and the primer may form any other structure that can disassociate from any DNA configuration of which it is a part.

Further, the primers used in this aspect of the present invention may be universal. In other words, each primer in the primers used in the reaction includes the same sequence (or a substantially similar sequence that allows amplification to occur). As is known to those of ordinary skill in the art, in standard PCR at least two different primers (i.e., having two different sequences) are used (i.e., a first set of primers, wherein each primer of the first set includes the same or similar sequence, and a second set of primers wherein each primer of the second set includes the same or similar sequence, that sequence being different from the sequence of the primers in the first set). The need for the two sets of primers is to provide for amplification using each of the single strands from the DNA. Thus, one strand will be replicated using primers from the first set. The second strand (which is complementary to the first strand) will also be replicated. However, as that second strand is complementary to the first strand, the primers of the second set may be complementary to the primers of the first set. This creates the problem of primer-dimers (when the primers hybridize to one another—rather than to the target template denatured DNA strands). However, in the present invention, each of the primers used have the same or similar sequence. There is no second set of complementary primers that is needed. As such, there are no other complementary primers for the primers of the present application to hybridize to, thus eliminating the problem of primer dimers. Further, as the end being extended is currently bound with the target region, self-annealing of product is eliminated. And, the original primer binding site on the target DNA region is open for binding of another primer.

While "at least one primer" and a site being "open for binding of another primer" are discussed herein, it will be recognized by those of ordinary skill in the art that the "at least one primer" and the "another primer" may have the same sequence (or substantially similar sequence) as it is known that PCR employs multiple copies of a primer for amplification of a target DNA sequence. Further, as is known to those of ordinary skill in the art, the reaction components generally include multiple copies of primers. Thus, it will be understood that "at least one primer" or "one primer" or "a primer" or "the primer" or like references may refer to a single primer, or a primer among a set of multiple copies of the same or similar primers. Further, while various PCR procedures described herein are discussed as amplifying DNA, those of ordinary skill in the art will recognize that does not limit the disclosure to those seeking DNA sequences, as procedures such as reverse transcription PCR are well known, wherein reverse transcriptase reverse transcribes RNA into cDNA, which is then amplified by PCR.

As described above, in one aspect, the primer or primers may be based on any sequence that is capable of forming a structure that allows or causes the primer to dissociate from a duplex form, such as under isothermic conditions. And, as described above, one such structure which allows such dissociation is a quadruplex structure. As previously discussed, such quadruplex structures are commonly formed by sequences rich in guanine residues. Thus, much of the discussion below is directed to G-rich sequences for primers, which are capable of forming such quadruplex structures. However, it will be appreciated by those of ordinary skill in the art that the general and particular sequences described below, and the particular structures, such as quadruplex structures, described below, are merely exemplary and that there may be other useful sequences that form structures which allow dissociation from a double-stranded DNA form in accordance with the principles of the present invention.

As is known to those of ordinary skill in the art, quadruplexes are high-ordered nucleic acid structures (DNA or RNA) formed from G-rich sequences that are built around tetrads of hydrogen bonded guanine bases. Thus, in order to provide primers that can form quadruplexes, the primers of this aspect of the present invention may be designed with a sequence having a G content of a high enough amount (or to obtain a high enough amount) to allow the primer to conform into a quadruplex structure, such as during an extension step of PCR. In one embodiment, the G content of the sequence of a primer of this aspect of the present invention is equal to or greater than 70%. In another embodiment, the G content may be equal to or greater than 75%. More specifically, in one embodiment, the primer may be an oligonucleotide having a sequence based on GGGTGGGTGGGTGGGT [SEQ. ID. NO. 1] ["(GGGT)$_4$"]. This sequence can form into a quadruplex. However, it will be recognized by those of ordinary skill in the art that primers for use in this aspect of the present invention do not have to include the exact (GGGT)$_4$ [SEQ. ID. NO. 1] sequence. By being "based on" the sequence (GGGT)$_4$ [SEQ. ID. NO. 1], those of ordinary skill in the art will recognize that substitutions and/or deletions may be made to this base sequence, so long as the resulting primer based on the (GGGT)$_4$ [SEQ. ID. NO. 1] sequence remains able to conform into a quadruplex structure, either on its own or during an extension step of a PCR process. For example, as described above, other sequences may form quadruplexes provided they include a guanine amount that is sufficient to form such quadruplexes. Further, the sequences do not have to be based on (GGGT)$_4$ [SEQ. ID. NO. 1], as there are other formulas that the sequences may be based on. One example of such a formula is d(G$_{3+}$N$_{1-7}$G$_{3+}$N$_{1-7}$G$_{3+}$N$_{1-7}$G$_3$).

In a particular embodiment, the at least one oligonucleotide primer is based on the sequence GGGTGGGTGGGTGGGT [SEQ. ID. NO. 1] ["(GGGT)$_4$"], which is capable of forming a very stable quadruplex, even in the presence of the complementary strand. The particular primers may be shorter versions of the (GGGT)$_4$ [SEQ. ID. NO. 1] sequence. These primers are thus unable to fold into a quadruplex on their own, but will fold into a quadruplex structure after polymerase elongation and dissociation from the target site, and will stay folded at annealing of the next cycle. Because QPA inhibits product self-annealing and increases the number of PCR cycles within the exponential growth phase, this aspect of the present invention improves efficiency of PCR by elongating the window of exponential amplification.

As described above, one aspect of the present invention includes the use of novel primers that form quadruplexes upon elongation. Quadruplexes are high-ordered DNA and RNA structures formed from G-rich sequences that are built around tetrads of hydrogen bonded guanine bases. The synthetic polynucleotides poly(dG) and poly(G) were determined to form four-stranded helical structures, with the G-tetrads stacked on one another, analogous to Watson-Crick base pairs in duplex DNA.

Quadruplexes can be formed from one, two, or four separate strands of DNA (or RNA) and can display a wide variety of topologies, which are in part a consequence of the various possible combinations of strand directions, as well as variations in loop size and sequence. They can be defined in general terms as structures formed by a core of at least two stacked G-tetrads, which are held together by loops arising from the intervening mixed sequence nucleotides that are not usually involved in the tetrads themselves. The combination of the number of stacked G-tetrads, the polarity of the strands, and the location and length of the loops would be expected to lead to a plurality of G quadruplex structures, as is found experimentally [as described in Burge, S. et al., Survey and Summary: *Quadruplex DNA: sequence, topology, and structure*, Nucleic Acids Research, 2006, Vol. 34, No. 19, pp. 5482-5415].

Quadruplex structures can be classified according to their strand polarities and the location of the loops that link the guanine strands for quadruplexes formed either from a single strand or from two strands. Adjacent linked parallel strands require a connecting loop to link the bottom G tetrad with the top G tetrad leading to what is referred to as "propeller"-type loops (these are also sometimes termed "strand-reversal" loops). This feature has been found both in crystal structures and in solution for quadruplexes formed from human telomeric DNA sequences and in a number of nontelomeric quadruplexes [as described in Burge, S. et al., Survey and Summary: *Quadruplex DNA: sequence, topology, and structure*, Nucleic Acids Research, 2006, Vol. 34, No. 19, pp. 5482-5415].

Quadruplexes are designated as "antiparallel" when at least one of the four strands is antiparallel to the others. This type of topology is found in the majority of bimolecular and many unimolecular quadruplex structures determined to date. Two further types of loops have been observed in these structures, in addition to parallel loops. "Lateral" (sometimes termed "edgewise") loops join adjacent G-strands. Two of these loops can be located either on the same or opposite faces of quadruplex, corresponding to head-to-head or head-to-tail, respectively, when in bimolecular quadruplexes. The second type of antiparallel loop, the "diagonal" loop joins opposite G-strands. In this instance, the directionalities of adjacent strands must alternate between parallel and antiparallel, and are arranged around a core of four stacked G-tetrads [as described in Burge, S. et al., Survey and Summary: *Quadruplex DNA: sequence, topology, and structure*, Nucleic Acids Research, 2006, Vol. 34, No. 19, pp. 5482-5415].

Further, in order to be detectable, such as for use in RT-PCR, the primer may have a label incorporated therein. Such a label may be chosen from labels that are known to those of ordinary skill in the art. Such labels include, but are not limited to, fluorescent labels. In one particular embodiment, the primer may have a fluorescent label incorporated therein. And in a particular embodiment, such a label may include 2Ap.

The inclusion of a label in the novel primer of the present invention overcomes many of the previously described drawbacks of current systems. As described above, RT-PCR quantification methods are based on the fact that the amount of target DNA produced and detected is directly proportional to the initial amount of sample DNA during the exponential growth phase. Since the fluorescence signal during the initial cycles is too weak to be distinguished from the background fluorescence (see the AB segment of FIG. 1) only a narrow window of the exponential growth phase is used for quantification (see the BC segment of FIG. 1). Thus, the efficiency of RT-PCR would be improved by reducing the background fluorescence (i.e., by the use of well-quenched probes before detection), and by a strong and immediate increase of fluorescence upon amplification, as well as by a longer exponential phase [as described in Edwards, K. J. et al. (2009) In Logan, J. et al. (eds.), *Real-time PCR*. Caister Academic Press, Norfolk, UK, pp. 85-93; Pfaffl, M. W. et al. (2009) In Logan, J. et al. (eds.), *Real-time PCR*. Caister Academic Press, Norfolk, UK, pp. 65-83].

As described above currently, four main probes are used to monitor real-time PCR [Lee, M. A., et al. (2009) In Logan, J. et al. (eds.), *Real-time PCR*. Caister Academic Press, Norfolk, UK, pp. 23-45]: (1) SYBR Green [Becker, A. et al. (1996) A quantitative method of determining initial amounts of DNA by polymerase chain reaction cycle titration using digital imaging and a novel DNA stain. *Anal Biochem*, 237, 204-207], (2) molecular beacons [Tyagi, S. et al. (1998) Multicolor molecular beacons for allele discrimination. *Nature biotechnology*, 16, 49-53; Tyagi, S. et al. (1996) Molecular beacons: probes that fluoresce upon hybridization. *Nature biotechnology*, 14, 303-308], (3) TagMan® probes [Holland, P. M. et al. (1991) Detection of specific polymerase chain reaction product by utilizing the 5'----3' exonuclease activity of *Thermus aquaticus* DNA polymerase. *Proc Natl Acad Sci USA*, 88, 7276-7280], and (4) Scorpion™ probes [Whitcombe, D. et al. (1999) Detection of PCR products using self-probing amplicons and fluorescence. *Nat Biotechnol*, 17, 804-807]. And, as described previously, there are drawbacks to each of these. SYBR Green is a dye that intercalates into double-stranded DNA nonspecifically resulting in fluorescence. Although SYBR Green is inexpensive, sensitive and easy to use, it also binds to any double-stranded DNA including non-specific products or primer dimers.

Figure 2:
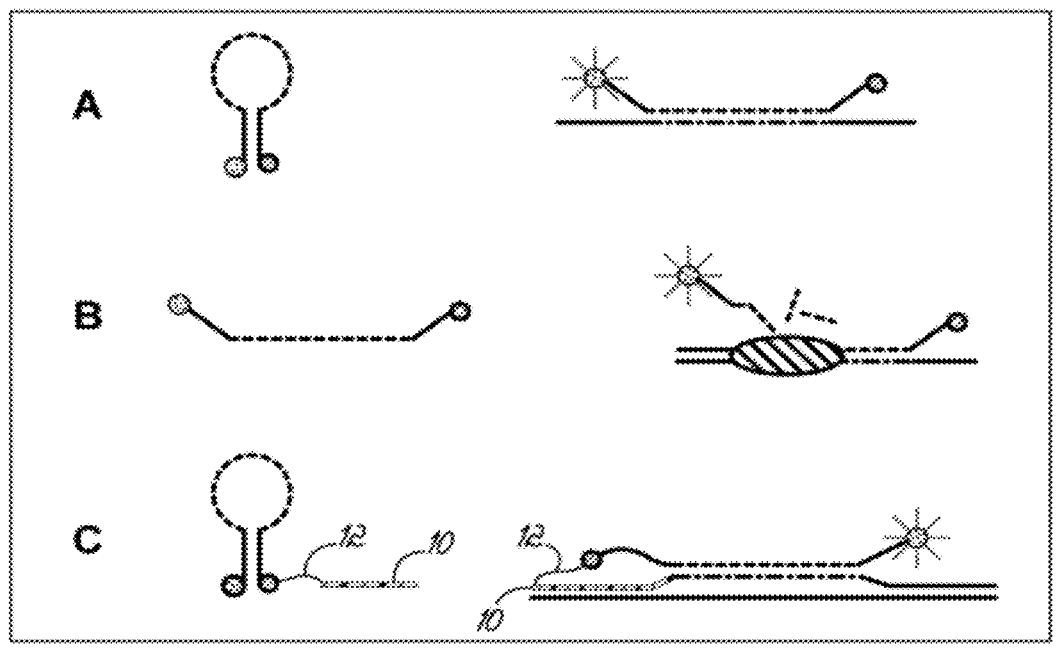
FIG. 2 is a schematic of structures and modes of action of previous probes with panel A showing a molecular beacon, panel B showing a TagMan®, and panel C showing a Scorpion™ probe.

Referring to FIG. 2, panel A, molecular beacons are single-stranded oligonucleotide probes that form a hairpin-shaped stem-loop structure. The loop contains a probe sequence (dashed line segment, FIG. 2, panel A) that is complementary to a target sequence in the PCR product. The stem is formed by the annealing of complementary sequences that are located on either side of the probe sequence. A fluorophore (dotted circle) and quencher (lined circle) are covalently linked to the ends of the hairpin. Upon hybridization to a target sequence the fluorophore is separated from the quencher and fluorescence increases. Hybridization usually occurs after unfolding of the hairpin and product duplexes in the denaturation step of the next PCR cycle.

As described above, there are several disadvantages with molecular beacons. First, they require two bulky and costly tags (fluorophore and quencher). Second, the assay requires a separate probe for each template (i.e. mRNA), which dramatically increases the design effort and expense. Third, the mechanism uses separate binding sites for primer and probe sequences. This introduces another component (probe oligonucleotide) to an already complex reaction, and adds additional design limitations due to the need to avoid interactions between the probe and primers. Fourth, hybridization of the probe requires heating steps to unfold the product duplex and hairpin. Consequently, molecular beacons can't be used under isothermal conditions. Fifth, design of the probes requires considerable effort and knowledge of nucleic acid thermodynamics. And sixth, probe hybridization involves a bimolecular probe-primer system. This makes the reaction entropically unfavorable, slows down hybridization and complicates product detection at exponential growth. The hybridization is much faster and efficient with monomolecular probe-primer system [as described in Whitcombe, D. et al. (1999) Detection of PCR products using self-probing amplicons and fluorescence. *Nat Biotechnol*, 17, 804-807].

Referring now to FIG. 2, panel B, TaqMan® probes are single-stranded unstructured oligonucleotides designed to be complementary to a PCR product. They have a fluorophore attached to the 5' end and a quencher coupled to the 3' end. When the probes are free in solution, or hybridized to a target the proximity of the fluorophore and quencher molecules quenches the fluorescence. During PCR, when the polymerase replicates a template on which a TagMan® probe is bound, the 5'-nuclease activity of the polymerase cleaves the probe. Upon cleavage, the fluorophore is released and fluorescence increases. The shortcomings listed above for molecular beacons hold true for TagMan®. An additional disadvantage of TagMan® probes is that they require the 5'-nuclease activity of the DNA polymerase used for PCR.

Referring now FIG. 2, panel C, Scorpion™ probes use a single oligonucleotide that consists of a hybridization probe (stem-loop structure similar to molecular beacons) and a primer (10) linked together via a non-amplifiable monomer (12). The hairpin loop contains a specific sequence that is complementary to the extension product of the primer (dashed line). After extension of the primer during the extension step of a PCR cycle, the specific probe sequence is able to hybridize to its complement within the extended portion when the complementary strands are separated during the denaturation step of the subsequent PCR cycle, and fluorescence will thus be increased (in the same manner as molecular beacons). Many of the shortcomings listed for molecular beacons hold true for Scorpion™ probes. First, they require two bulky and costly tags (fluorophore and quencher). Second, the assay requires a separate probe for each template (i.e. mRNA), which dramatically increases the design effort and expense. Third, the mechanism uses separate binding sites for primer and probe sequences. This introduces another component (probe oligonucleotide) to an already complex reaction, and adds additional design limitations due to the need to avoid interactions between the probe and primers. Fourth, hybridization of the probe requires heating steps to unfold the product duplex and hairpin. Consequently, molecular beacons can't be used under isothermal conditions. And fifth, design of the probes requires considerable effort and knowledge of nucleic acid thermodynamics.

Figure 3:
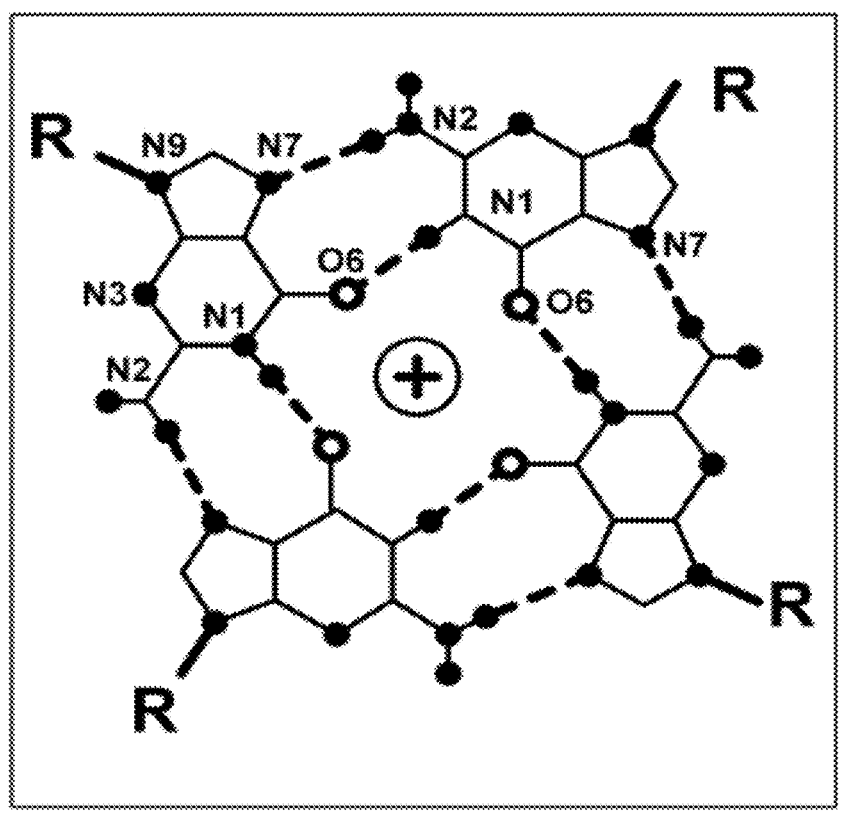
FIG. 3 is a schematic of a DNA G-quartet.

In one aspect, the primer(s) may be based on any sequence that is capable of forming a quadruplex structure (or other non-B DNA conformation or other DNA structure in which intramolecular base-pairing allows or causes the primer to dissociate from a double-stranded DNA and form the particular structure such as during an extension step of PCR). Non-B DNA conformations include triplexes. As is known to those of ordinary skill in the art, due to their base pairing properties, nucleic acid sequences can often form specific structures under certain solution conditions. For example, in the presence of certain metal ions (e.g., $K^+$), short guanine (G)-rich sequences fold into a structure known as a G-quartet or quadruplex (see FIG. 3). Quadruplexes are very stable and biophysical studies have shown that they possess intrinsic optical properties (e.g., absorb light at 300 nm) that distinguish them from other secondary structures. Previously, quadruplex-formation assays have been developed, which exploit this unique quadruplex signature to study enzymes that cleave DNA (Kankia, B. I. (2006) *A real-time assay for monitoring nucleic acid cleavage by quadruplex formation*, Nucleic acids research, 34, e141) or facilitate strand-exchange reactions (Kankia, B. I. (2004) *Optical absorption assay for strand-exchange reactions in unlabeled nucleic acids*, Nucleic acids research, 32, e154). Briefly, when G-rich sequences with the potential to form a quadruplex are incorporated into DNA substrates they are initially in the quenched state. Upon enzymatic activity (i.e., strand cleavage or strand-exchange) the released sequence folds into a quadruplex and becomes visible when monitored by absorption or fluorescence spectroscopy.

One aspect of the present invention, then, uses the free energy of DNA quadruplexes (or other non-quadruplex conformations) to drive unfavorable (endergonic) reactions of nucleic acids (e.g., isothermal PCR). The key point of such reactions is that some sequences—e.g., some G-rich sequences—are capable of forming quadruplexes (or other conformations) with significantly more favorable thermodynamics than the corresponding DNA duplexes. The sequences are incorporated within DNA duplexes, which after interaction with an initiator (e.g., DNA polymerase) self-dissociate from the complementary strand and fold into quadruplexes (or other conformations). The energy of formation of the non B-DNA structure, or other DNA structure is used to drive PCR at substantially constant temperature.

Thus, in certain embodiments, the primer may include a sequence that is generally based on a sequence in the form of $d(G_{3+}N_{1-7}G_{3+}N_{1-7}G_{3+}N_{1-7}G_3)$ and include a label. In another embodiment, the primer may include a sequence that is generally based on the $(GGGT)_4$ [SEQ. ID. NO. 1] sequence and includes a label such as 2Ap. And so, at least a portion of the primer sequence may have a sequence based on 2Ap-G3T (GGG2ApGGGTGGGTGGG) [SEQ. ID. NO. 10]. However, it will be recognized by those of ordinary skill in the art that this sequence is not necessarily the entire sequence of the primer, merely that the primer may include the sequence based on 2Ap-G3T [SEQ. ID. NO. 10] as a portion of the overall sequence of the primer, And so, this aspect of the present invention also provides a primer, wherein the portion of the primer sequence based on 2AP-G3T [SEQ. ID. NO. 10] is attached to another sequence specific for use as a primer to detect a desired target nucleic acid sequence.

Figure 4:
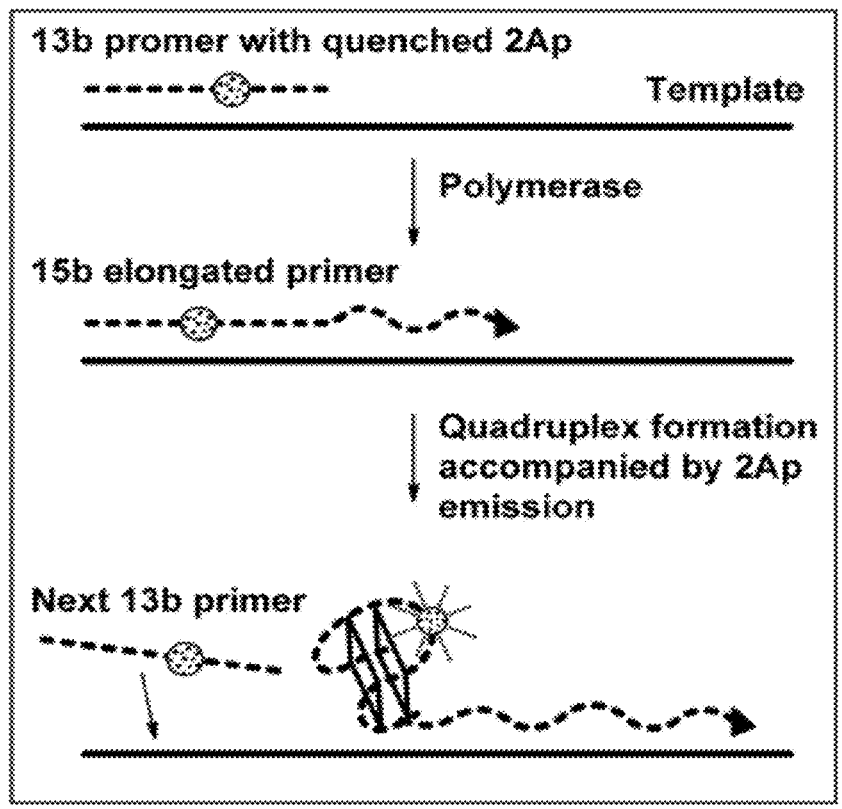
FIG. 4 is a schematic illustration of the QPA process.
Figure 5:
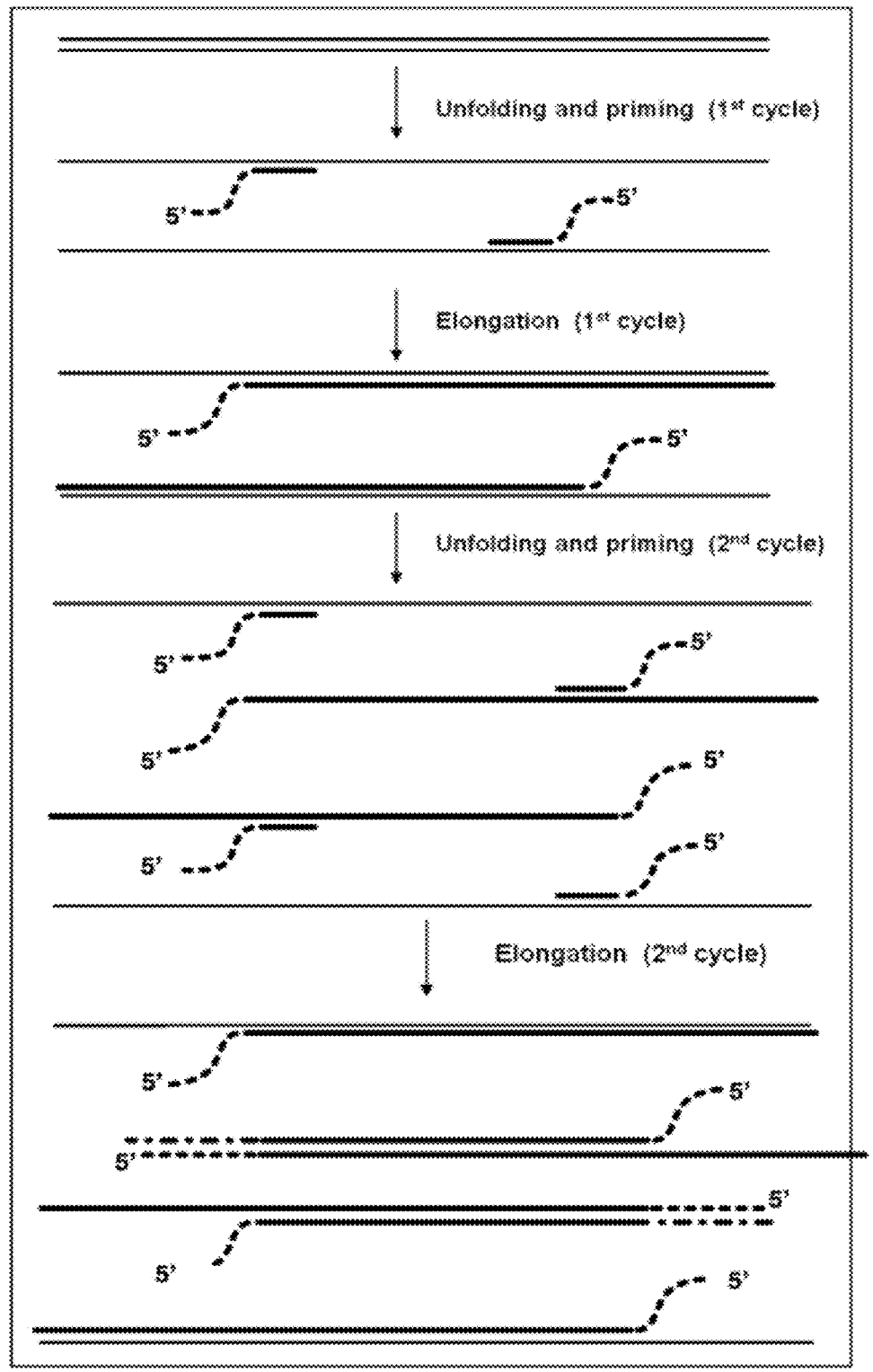
FIG. 5 shows the incorporation of the QPA target site (dotted lines) in templates by attachment of quadruplex forming sequences (dashed lines) to primers.

And so, the problems with present nucleic acid amplification, detection, and quantification systems and methods are overcome by the presently described amplification process. Referring to FIG. 4, the general principle of the amplification process is shown. The process uses specific primers designed to fold into monomolecular quadruplexes upon elongation with significantly more favorable thermodynamics than the corresponding DNA duplex. In particular, in the illustrated embodiment, a primer that is a truncated version of $(GGGT)_4$ [SEQ. ID. NO. 1] (a 13b primer in the illustrated embodiment) and incorporates 2Ap is used. In another particular embodiment, this primer has the sequence GGG(2Ap)GGGTGGGTGGG (2Ap-G3T) [SEQ. ID. NO. 10] When this primer is not in the quadruplex conformation, fluorescence of 2Ap is quenched. In alternate embodiments, the primer may include different, albeit similar, sequences. For example, in one alternate embodiment, the primer may have the sequence GGG(2Ap)GGGTGGGTGG [SEQ. ID. NO. 11]. And in another alternate embodiment, the primer may have the sequence GGG(2Ap)GGGTGGGTG [SEQ. ID. NO. 12] (as in the illustrated embodiment). As can be seen in the top panel of FIG. 4, before elongation, the primers (here shown as a 13b primer e.g., GGG(2Ap) GGGTGGGTG [SEQ. ID. NO. 12]) form duplexes with the target sequence since they are missing a few guanine residues that would result in quadruplex formation. Under PCR conditions, elongation then begins, with the DNA polymerase adding dNTPs to the end of the primers (as shown in the second panel of FIG. 4). This elongation then eventually adds the length and/or guanine residues necessary to allow a quadruplex structure to be formed. Once this occurs (see the third panel of FIG. 4), the 5'-end of each product DNA is trapped in a quadruplex and its complementary sequence (the target DNA) is fully accessible to another incoming primer. And with the formation of the quadruplex, 2Ap is no longer quenched. In still further embodiments, the primers may have the sequence GG(2Ap)TGGTGTGGTTGG [SEQ. ID. NO. 24] or may have the sequence GGTTGG(2Ap) GTGGTTGG [SEQ. ID. NO. 20]. Again, while this process may be referred to herein as "QPA," and while the schematic in FIG. 5 is described as showing "QPA," those of ordinary skill in the art will recognize that the aspects of the present invention are not limited to primer sequences that form quadruplexes (as described previously).

Thus, the amplification process of the present invention has the potential to expand the exponential growth phase of the reaction, because product self-annealing is eliminated due to the manner of the reaction (as shown in FIG. 4). As a result, the DNA yield can increase dramatically since each extra cycle will double the amount of product DNA. A longer exponential growth phase will also be very useful for DNA quantification by RT-PCR, as will be described in greater detail below. In addition, the amplification process using primers such as described herein has the potential to eliminate non-specific products. Specifically, decreasing the annealing temperature can enhance product refolding. This would reduce the availability of single-stranded regions for non-specific priming and further improve specific priming at target sites constantly available for the primers.

Further, since the conformation taken on by the primer sequence (such as a quadruplex) is more stable than its corresponding duplex, unfolding of the duplex or release of target for the incoming primers can occur without the need of substantial temperature change or any temperature change. In other words, in standard PCR, following the extension step, the DNA is in a duplex form. The next cycle then begins by raising the temperature to a point that the double-stranded DNA again denatures (i.e., separates into single strands). This is necessary in order to provide the separated sense and anti-sense single-stranded DNA strands for primer binding (to each of the strands), followed by elongation during the next extension step (once the temperature of the reaction is reduced). However, by using primers based on a sequence, such as the (GGGT)$_4$ [SEQ. ID. NO. 1] sequence, the primers and extending nucleotides that are added during the extension step naturally conform into a structure such as a quadruplex. As this occurs, the primer (e.g., forming the quadruplex structure) naturally separates from the target DNA sequence complementary to the primer, thereby leaving the target region complementary to the primer exposed in single-stranded form for binding of the next primer. This occurs without requiring raising of the temperature to denature the strands from one another. Thus, amplification can proceed under isothermal conditions. And so, the isothermal DNA amplification provided by the present invention does not require expensive instrumentation for thermocycling and may allow DNA amplification in the field and at point-of-care.

Thus, another aspect of the present invention provides an isothermic process for amplifying at least one target nucleic acid sequence contained in a nucleic acid or a mixture of nucleic acids. The process includes treating a nucleic acid or a mixture of nucleic acids with at least one primer, such as an oligonucleotide primer, adapted to conform into a structure that can dissociate from a DNA duplex structure in the absence of heating [i.e., the primer includes a sequence that naturally conforms into a structure, such as a quadruplex structure (or any other non-B DNA configuration or other DNA structure) in which intramolecular base pairing allows or causes the primer to dissociate from the double stranded DNA—of which it is one strand—and form its particular structure]. For example, the primer may be adapted to conform into a quadruplex structure during an extension step of a polymerase chain reaction, under isothermic conditions. During this isothermic process, for the at least one nucleic acid sequence being amplified, an extension product of the at least one primer is synthesized which is complementary to a strand from the nucleic acid or mixture of nucleic acids. In this process, the at least one primer is selected so as to be sufficiently complementary to the strand from the nucleic acid or a mixture of nucleic acids to hybridize therewith such that the extension product synthesized from the at least one primer, when it is separated from its complement, can serve as a template for further synthesis of an extension product of another primer.

Thus, formation of the quadruplex, or other conformation, occurs spontaneously in parallel to elongation and as a result, amplification can proceed under isothermal conditions. As such, isothermal DNA amplification does not require expensive instrumentation for thermocycling and allows DNA amplification in the field and at point-of-care. Several versions of isothermal DNA amplification have previously been developed [see Tomita, N. et al. (2008) Loop-mediated isothermal amplification (LAMP) of gene sequences and simple visual detection of products. *Nature protocols,* 3, 877-882; Vincent, M., et al. (2004) Helicase-dependent isothermal DNA amplification. *EMBO reports,* 5, 795-800; Andras, S. C. et al. (2001) Strategies for signal amplification in nucleic acid detection. *Molecular biotechnology,* 19, 29-44; Walker, G. T. et al. (1992) Strand displacement amplification—an isothermal, in vitro DNA amplification technique. *Nucleic acids research,* 20, 1691-1696; Walker, G. T. et al. (1992) Isothermal in vitro amplification of DNA by a restriction enzyme/DNA polymerase system. *Proceedings of the National Academy of Sciences of the United States of America,* 89, 392-396; Fox, J. D. et al. (2009) In Logan, J. et al. (eds.), *Real-time PCR.* Caister Academic Press, Norfolk, UK, pp. 163-175]. However, all these existing systems require extra reaction components or polymerases with specific activities, whereas QPA does not.

The process described above may further include separating the primer extension products from the templates on which they were synthesized to produce single-stranded molecules. And, the process may further include treating the single-stranded molecules with the at least one primer under isothermic conditions such that a primer extension product is synthesized using each of the single strands as a template.

The primers used in this isothermic application may be the primers adapted to form quadruplexes, as described above. Thus, the primers may be designed with a sequence having a G content of an amount (or to obtain a high enough amount) such that the primer conforms into a quadruplex structure during an extension step of PCR. In one embodiment, the G content of the sequence of a primer of this aspect of the present invention is equal to or greater than 70%. In another embodiment, the G content may be equal to or greater than 75%. More specifically, in one embodiment, the primer may be an oligonucleotide having a sequence based on GGGTGGGTGGGTGGGT [SEQ. ID. NO. 1] ["(GGGT)$_4$"]. However, it will be recognized by those of ordinary skill in the art that primers for use in this aspect of the present invention do not have to include the exact (GGGT)$_4$ [SEQ. ID. NO. 1] sequence. As described above, other sequences may form quadruplexes provided they include a guanine amount that is sufficient to form such quadruplexes. And, as described above, the primers do not have to have sequences that form quadruplexes. Rather, any primer adapted to conform into a structure that can dissociate from a DNA duplex structure in the absence of heating will suffice for the principles of the present invention [i.e., the primer includes a sequence that naturally conforms into a structure, such as a quadruplex structure (or any other non-B DNA configuration or other DNA structure) in which intramolecular base pairing allows or causes the primer to dissociate from the double stranded DNA—of which it is one strand—and form its particular structure].

Further, in order to be detectable, such as for use in RT-PCR, the primer may have a label incorporated therein. Such a label may be chosen from labels that are known to those of ordinary skill in the art. Such labels include, but are not limited to, fluorescent labels. In one particular embodiment, the primer may have a fluorescent label incorporated therein. And in a particular embodiment, such a label may include 2Ap. However, other fluorescent nucleotides may include pteridine analogs: 3-methyl isoxanthopterin (3MI) (Ex348, Em431), 6-methylisoxanthopterin (6MI) (Ex340, Em430) and (4-amino-6-methyl-8-(2¢-deoxy-â-D-ribofuranosyl)-7(8H)-pteridone (6AMP) (Ex330, Em435).

Thus, in certain embodiments, the primer may include a sequence that is generally based on the (GGGT)$_4$ [SEQ. ID. NO. 1] sequence and includes a label such as 2Ap. And so, at least a portion of the primer sequence may have a sequence based on 2Ap-G3T [SEQ. ID. NO. 10]. For example, one such primer may have the sequence GGG2ApGGGTGGGTGGG (2Ap-G3T) [SEQ. ID. NO. 10]. However, it will be recognized by those of ordinary skill in the art that this sequence is not necessarily the entire sequence of the primer, merely that the primer may include the sequence based on 2Ap-G3T [SEQ. ID. NO. 10] as a portion of the overall sequence of the primer, And so, this aspect of the present invention also provides a primer, wherein the portion of the primer sequence based on 2Ap- G3T [SEQ. ID. NO. 10] is attached to another sequence specific for use as a primer to detect a desired target nucleic acid sequence.

Another unique property of the amplification process and primers disclosed herein is that 2Ap incorporated in the primers results in strong fluorescence emission upon formation of a structure such as a quadruplex, as will be described in greater detail below, thus serving as a sensitive real-time detection probe.

Further, as described above, a drawback of current RT-PCR-specific quantification systems is that they use FRET-based applications, which require costly synthesis and considerable effort to design a sensitive probe. A quantification mechanism that uses intrinsic fluorescence of primers will significantly simplify the detection process. And so, another aspect of the present invention provides a quadruplex forming sequence with incorporated 2Ap (2Ap-G3T) that emits strong fluorescence upon formation of a structure such as a quadruplex. Thus, another aspect of the present invention provides a QPA-based real-time quantification system (RT-QPA) using 2Ap as a sensitive probe for quantification.

More specifically, another aspect of the present invention provides a real-time quantification PCR method for detecting amplification of a target nucleic acid. The method includes treating a nucleic acid or a mixture of nucleic acids with at least one primer, such as an oligonucleotide primer, adapted to conform into a structure that can dissociate from a DNA duplex structure in the absence of heating, such as into a quadruplex structure during an extension step of an amplification reaction, such as RT-PCR polymerase chain reaction. In the method, the at least one primer includes a label that is quenched when the at least one primer is in a non-dissociative conformation (like a non-quadruplex conformation) and that is detectable when the at least one primer is in a dissociative conformation (like a quadruplex conformation).

Further, in order to be detectable, such as for use in RT-PCR, the primer may have a label incorporated therein. Such a label may be chosen from labels that are known to those of ordinary skill in the art. Such labels include, but are not limited to, fluorescent labels. In one particular embodiment, the primer may have a fluorescent label incorporated therein. And in a particular embodiment, such a label may include 2Ap.

Thus, in certain embodiments, the primer may include a sequence that is generally based on the (GGGT)$_4$ [SEQ. ID. NO. 1] sequence and includes a label such as 2Ap. And so, at least a portion of the primer sequence may have a sequence based on 2Ap-G3T [SEQ. ID. NO. 10]. For example, one such primer may have the sequence GGG2ApGGGTGGGTGGG (2Ap-G3T) [SEQ. ID. NO. 10]. However, it will be recognized by those of ordinary skill in the art that this sequence is not necessarily the entire sequence of the primer, merely that the primer may include the sequence based on 2Ap-G3T [SEQ. ID. NO. 10] as a portion of the overall sequence of the primer, And so, this aspect of the present invention also provides a primer, wherein the portion of the primer sequence based on 2Ap-G3T [SEQ. ID. NO. 10] is attached to another sequence specific for use as a primer to detect a desired target nucleic acid sequence. And, again, the G-rich sequences described herein are merely exemplary.

Thus, after polymerase elongation, the specifically designed guanine-rich primers are capable of forming quadruplexes with significantly more favorable thermodynamics than the corresponding DNA duplexes. As a result, target sequences are always accessible for the primers since their complementary strands are trapped in a dissociative conformation (such as a quadruplex) and DNA amplification can proceed under isothermal conditions. In addition, 2Ap nucleotides incorporated and fully quenched within the primers regain maximum emission upon quadruplex formation allowing very simple and accurate detection of product DNA. Thus, the amplification process described herein (i) lacks a product self-annealing; (ii) can proceed under isothermal conditions; and (iii) uses intrinsic fluorescence of primers for quantification of DNA products.

Thus, to eliminate the drawbacks inherent in the presently used molecular beacons, TagMan®, and Scorpion™ probes, the present invention provides, in one exemplary embodiment, QPA for use in RT-PCR (referred to herein as RT-QPA). Again, while "QPA" and "RT-QPA" is used herein, those of ordinary skill in the art will recognize that the amplification process and primers are not limited to those that form quadruplexes—but include sequences that form any dissociative structures. RT-QPA is based on fluorescence of 2Ap incorporated within the QPA primers. As described above, 2Ap is a fluorescent analog of adenine, which forms Watson-Crick base-pairs with thymidine [Law, S. M. et al. (1996) Spectroscopic and calorimetric characterizations of DNA duplexes containing 2-aminopurine. *Biochemistry*, 35, 12329-12337; McLaughlin, L. W. et al. (1988) A new approach to the synthesis of a protected 2-aminopurine derivative and its incorporation into oligodeoxynucleotides containing the Eco RI and Bam HI recognition sites. *Nucleic Acids Res*, 16, 5631-5644] and is well tolerated by DNA polymerases [Fidalgo da Silva, E. et al. (2002) Using 2-aminopurine fluorescence to measure incorporation of incorrect nucleotides by wild type and mutant bacteriophage T4 DNA polymerases. *The Journal of biological chemistry*, 277, 40640-40649]. Free 2Ap has a very high quantum yield (0.68) which is ~100-fold reduced upon incorporation into a DNA duplex [Ward, D. C. et al. (1969) Fluorescence studies of nucleotides and polynucleotides. I. Formycin, 2-aminopurine riboside, 2,6-diaminopurine riboside, and their derivatives. *J Biol Chem*, 244, 1228-1237]. Unfolding of the DNA duplex into complementary single-strands is typically accompanied by only a several-fold increase in fluorescence [Law, S. M. et al. (1996) Spectroscopic and calorimetric characterizations of DNA duplexes containing 2-aminopurine. *Biochemistry*, 35, 12329-12337; Menger, M. et al. (1996) Mg(2+)-dependent conformational changes in the hammerhead ribozyme. *Biochemistry*, 35, 14710-14716; Rist, M. et al. (2001) Association of an RNA kissing complex analyzed using 2-aminopurine fluorescence. *Nucleic Acids Res*, 29, 2401-2408]. Thus, the fluorescence of 2Ap present in single strands is significantly quenched, which limits the sensitivity of the probe. Studies that developed the present invention show that the fluorescence of 2Ap incorporated into the loop regions of a quadruplex display fluorescence emission comparable to that of free 2Ap. Thus, RT-QPA primers with intrinsic fluorescence represent simple and very sensitive probes for quantification of DNA amplicons, and have the potential to overcome the shortcomings of traditional detection methods discussed above.

Thus, the advantages of RT-QPA are many. First, there is the reduced expense of 2Ap containing primers relative to chemical synthesis of separate probes with dye-quencher pairs. Second, the primer-probe for any mRNA is universal. Third, since the detection probe is part of the primer, QPA is free from complications introduced by separate probe sequences. Fourth, the mechanism does not require special enzymatic activity of a polymerase or heating steps. The detection can be performed under isothermal conditions. Fifth, the primer is universal for any PCR reaction, which completely eliminates the primer-probe design step. And sixth, the mechanism is truly monomolecular which guarantees immediate signal increase at the initial stage of the amplification process and efficient detection of early cycles invisible in the case of bi-molecular detection mechanisms.

Figure 13:
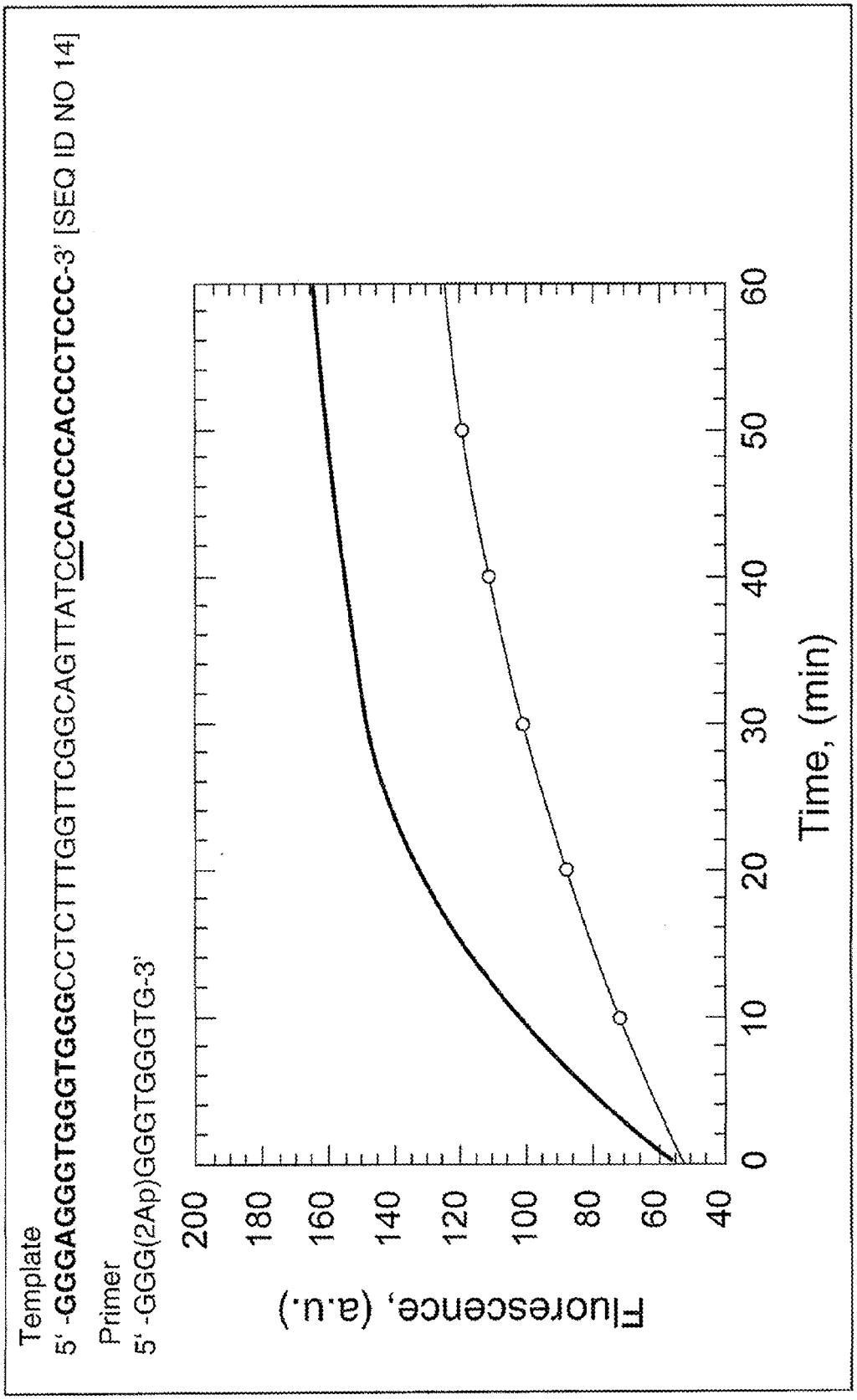
FIG. 13 shows isothermal QPA at 55° C. at 50 nM (black line) and 5 nM (-o-) template, 1 µM primer, 200 µM dNTPs and 5 U Taq in 100 µl buffer indicated in FIG. 11.

In addition, RT-QPA is extremely specific since specificity is not determined only by binding to a specific target, but also by proper elongation of the next few bases to create a quadruplex. For instance, the reaction shown in FIG. 13 uses two cytidines (underlined) adjacent to the target sequence (bold type at 3' end). It is known that quadruplexes can't tolerate nucleotide substitutions in G-tracts [Kankia, B. I. (2004) Optical absorption assay for strand-exchange reactions in unlabeled nucleic acids. *Nucleic Acids Res*, 32, p. 154]. Thus, to produce a false signal, non-specific priming alone is not enough; the non-specifically bound primer would also have to bind at cytidine-tracts.

As will be appreciated by those of ordinary skill in the art, naturally-occurring target DNA will not necessarily include a sequence complementary to the primer sequence (e.g., will not necessarily include a sequence based on $(GGGT)_4$ [SEQ. ID. NO. 1] or other dissociative sequence). And so, the DNA templates need to have incorporated target sequences, which can be accomplished by 2 cycles of traditional PCR. The incorporation of the target sequence into a template is shown schematically in FIG. 5. The quadruplex folding sequence (dashed lines) will be attached at the 5'-end of both forward and reverse primers. The products of the 2nd cycle (four duplexes at the end of PCR, FIG. 5) contain two single-stranded amplicons fully complementary to each other with incorporated target sites at the 3'-end (dotted lines). Thus, at the end of the 2nd cycle, the number of amplicons with incorporated target sites equals the initial amount of template, which is important for DNA quantification. At this point, the primer will be added to the mix and amplification may be continued under isothermal cycling conditions (although traditional thermal cycling conditions may also be used). Thereafter, the process will amplify only the desired short templates, neglecting the other six unwanted templates which usually are amplified in traditional PCR.

Thus, to incorporate target sequences within templates, an extra step of traditional PCR is required. However, difficulties at this step are not expected, since only two cycles will be performed under favorable conditions for PCR exponential growth: high concentration ratio of primer over template. Moreover, as described above, one aspect of the present invention is that the entire process is isothermal. As used herein, "isothermal" not only encompasses PCR that is truly isothermal (i.e., does not include any raising or lowering of temperatures, such as in a thermal cycle), but also encompasses PCR including an initial cycle or couple of cycles or few cycles that are used to incorporate the target sequences into the DNA template, as described above (and as shown schematically in FIG. 5, for example). In the case of RT-QPA, (i.e. gene expression studies) no extra step is necessary since the target site can be incorporated during cDNA synthesis.

The various aspects of the present invention will be described in greater detail with respect to the following Examples.

EXAMPLE 1

Example 1 describes preliminary studies that were designed and performed regarding the requirements of QPA and the design of the primers, to determine the optical and thermodynamic properties of the quadruplex-forming sequence.

Requirements of QPA and Design of the Primers.

According to the QPA mechanism (FIG. 4), primers should dissociate from a target site and fold into a monomolecular quadruplex following polymerase elongation. To do so, the quadruplex should be thermodynamically more stable than the corresponding DNA duplex. At the same time, the QPA mechanism also assumes that the primers (shorter versions of the quadruplex sequence) readily form duplexes with the target site (a prerequisite for DNA polymerase activity). It is also desirable that the sequences tolerate base substitutions of fluorescent analogs and emit a fluorescence signal upon quadruplex formation for real-time quantification of the product.

Thus, a successful QPA primer should comply with the following requirements: (i) bind to the target site, (ii) upon elongation dissociate from the target site and form a quadruplex, and (iii) emit light during the structural rearrangement. And so, this Example focused on the $(GGGT)_4$ [SEQ. ID. NO. 1] sequence which folds into a stable monomolecular quadruplex in the presence of $K^+$ [as described in Jing, N., Rando, R. F., Pommier, Y. and Hogan, M. E. (1997) *Ion selective folding of loop domains in a potent anti-HIV oligonucleotide*, Biochemistry, 36, 12498-12505, incorporated by reference herein in its entirety].

Optical and Thermodynamic Properties of Quadruplex Forming Sequence.

As described above, a unique property of QPA is that 2Ap incorporated in the primers results in strong fluorescence emission upon quadruplex formation, thus serving as a sensitive real-time detection probe. UV melting studies as a function of DNA strand concentration have shown that $(GGGT)_4$ [SEQ. ID. NO. 1] folds into a monomolecular structure ($T_m$ doesn't depend on strand concentration) that was unusually stable. For instance, in the presence of 50 mM KCl and 2 mM $MgCl_2$, the $(GGGT)_4$ [SEQ. ID. NO. 1] quadruplex melts above 100° C. Removal of the terminal thymidine did not change the CD profile of the quadruplex (see FIG. 6, -□-). Therefore, in further experiments, the truncated sequence $(GGGT)_3GGG$ [SEQ. ID. NO. 2] was used. To establish appropriate positions for 2Ap, a $(GGGT)_3GGG$ sequence with T→2Ap substitutions at the 4th position [SEQ. ID. NO. 10] was also studied, which didn't reveal any change in CD profile (see FIG. 6, -○-), demonstrating that the quadruplex will tolerate 2Ap nucleotides at these positions [a $(GGGT)_3GGG$ sequence with T→2Ap substitutions at the $4^{th}$ and $12^{th}$ positions was also studied, without any change in CD profile]. T→2Ap substitution in the 4th position revealed a striking fluorescence effect: upon formation of GGG(2Ap)GGGTGGGTGGG (2Ap-G3T) [SEQ. ID. NO. 10], the fluorescence emission of 2Ap reaches the level of its free state (see FIG. 7).

Thus, in experiments, a construct with incorporated 2Ap as follows was used: GGG(2Ap)GGGTGGGTGGG ["2Ap-G3T"] [SEQ. ID. NO. 10], GGG(2Ap)GGGTGGGTGG [SEQ. ID. NO. 11] ["G3T-ss14"], GGG(2Ap)GGGTGGGTG [SEQ. ID. NO. 12] ["G3T-ss13"], GGG(2Ap)GGGTGGGTGGG [SEQ. ID. NO. 10] in duplex with its complementary strand CCCACCCACCCTCCC [SEQ. ID. NO. 3] ["G3T-ds15"], and GGG(2Ap)GGGTGGGTG [SEQ. ID. NO. 12] in duplex with a complementary strand CCCACCCACCCTCCC [SEQ. ID. NO. 3].

Principle of QPA

Role of Cations and Terminal Guanines in Quadruplex Formation.

Figure 8:
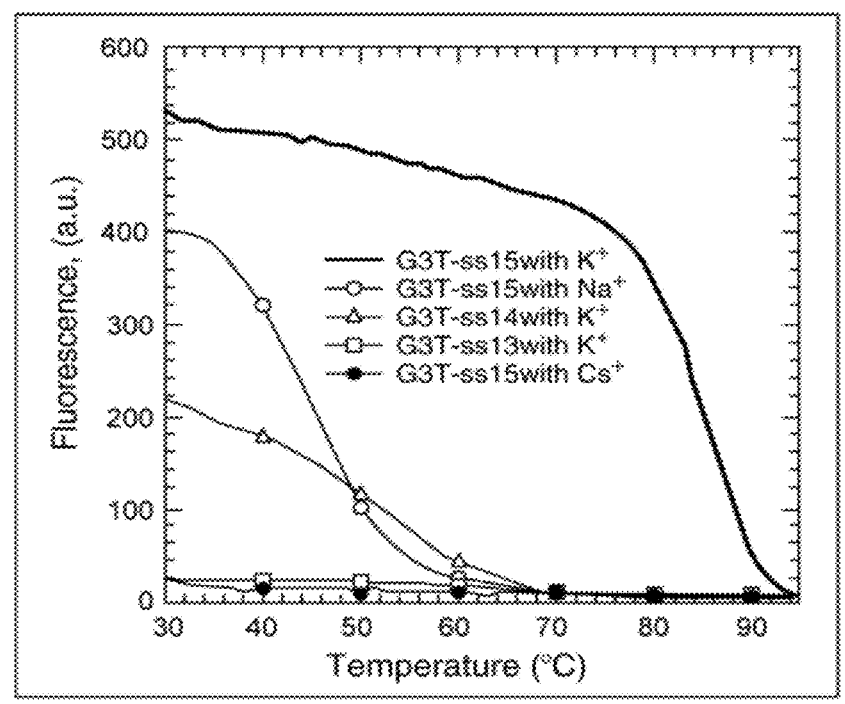
FIG. 8 shows fluorescence melting curves of single-stranded oligonucleotides, where G3T-ss15 is 2Ap-G3T [SEQ. ID. NO. 10], G3T-ss14 is GGG(2Ap)GGGTGGGTGG [SEQ. ID. NO. 11], and G3T-ss13 is GGG(2Ap)GGGTGGGTG [SEQ. ID. NO. 12] in 50 mM monocations.

FIG. 8 demonstrates fluorescence unfolding experiments of G3T-ss15 [SEQ. ID. NO. 10], G3T-ss14 [SEQ. ID. NO. 11], and G35-ss13 [SEQ. ID. NO. 12]. Unfolding of G3T-ss15 [SEQ. ID. NO. 10] was performed in the presence of 50 mM monovalent cations, $Na^+$ (-○-), $K^+$ (black line) and $Cs^+$ (-●-). In the case of Na+ ions the melting curve reveals the sigmoidal behavior characteristic of monophasic transition with $T_M$ ~45° C. The transition corresponds to unfolding of the quadruplex, which is accompanied by quenching of 2Ap fluorescence by adjacent guanines in the unfolded quadruplex. As expected [as shown by Jing, N., Rando, Pommier, Y. and Hogan, M. E. (1997) *Ion selective folding of loop domains in a potent anti-HIV oligonucleotide*, Biochemistry, 36, 12498-12505], the potassium salt of G3T-ss15 is very stable with a $T_M$ of ~88° C. (black line). Thus, both $Na^+$ and $K^+$ ions are able to fold quadruplexes, however the latter is almost 45° C. more stable. In the presence of $Cs^+$ ions G3T-ss15 [SEQ. ID. NO. 10] does not reveal any measurable fluorescence over the entire temperature range, which suggests that $Cs^+$ does not support quadruplex formation [Kankia, B. I. and Marky, L. A. (2001) *Folding of the thrombin aptamer into a G-quadruplex with Sr(2+): stability, heat, and hydration*, Journal of the American Chemical Society, 123, 10799-10804]. The results are in agreement with observations that $K^+$ ions with ionic radii of 1.33 Å are the optimum size for a cation to enter the inner core of G-quartets, while $Cs^+$ ions with ionic radii of 1.69 Å are too big [Jing, N., Rando, R. F., Pommier, Y. and Hogan, M. E. (1997) *Ion selective folding of loop domains in a potent anti-HIV oligonucleotide*, Biochemistry, 36, 12498-12505].

The role of terminal guanines in quadruplex formation in the presence of $K^+$ ions was studied similarly. Deletion of a single guanine at the 3'-end, G3T-ss14 [SEQ. ID. NO. 11], significantly destabilized the quadruplex (FIG. 8, -Δ-). However, it is still able to create some structure at lower temperatures. Deletion of another guanine, G3T-ss13 [SEQ. ID. NO. 12], almost completely inhibits quadruplex formation (-□-). Thus, the experiments shown in FIG. 8 suggest that (i) in the presence of $Cs^+$ ions mixing of full-length G3T-ss15 [SEQ. ID. NO. 10] to its complementary sequence should result in a DNA duplex; and (ii) in the presence of $K^+$ ions the truncated variant, G3T-ss13 [SEQ. ID. NO. 12], should also be able to form a duplex.

Role of Cations and Terminal Guanines in Duplex Formation.

Figure 9:
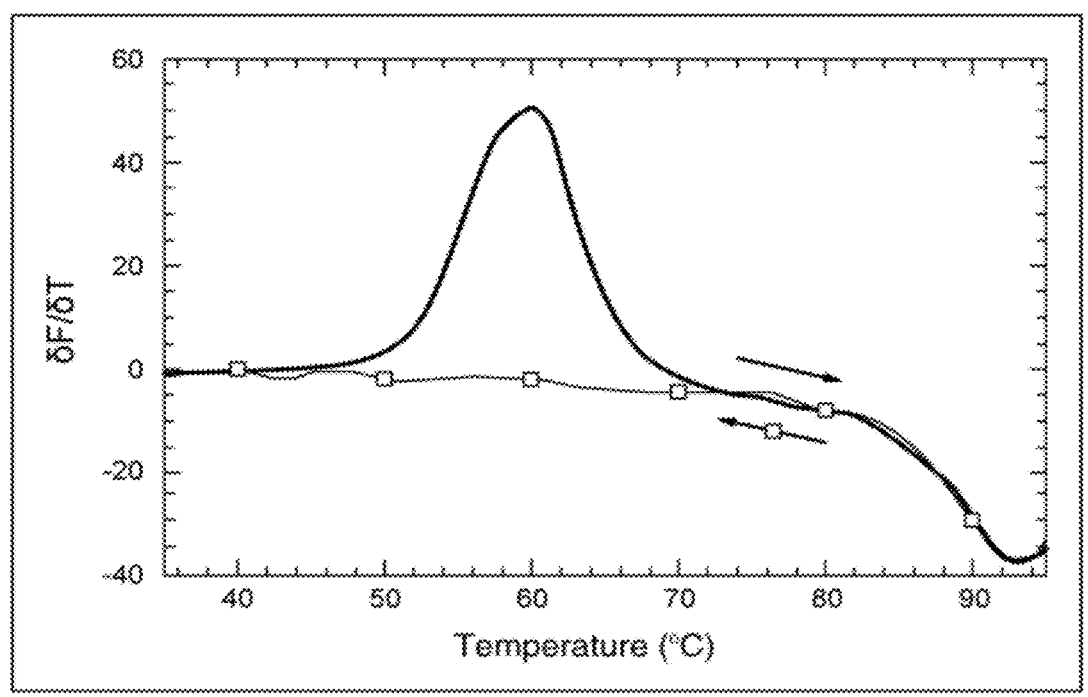
FIG. 9 shows fluorescence melting curves of G3T-ds15 duplex (i.e., GGG(2Ap)GGTGGGTGGG ("2Ap-G3T") [SEQ. ID. NO. 10] in duplex form with its complementary strand CCCACCCACCCTCCC [SEQ. ID. NO. 3]), wherein the black and squared lines correspond to heating and cooling (at 1° C./min rate), respectively.

To mimic DNA conformational changes that take place upon the QPA reaction, the fluorescence melting of the G3T-ds15 [SEQ. ID. NO. 10] duplex was studied in amplification buffer (15 mM KCl, 35 mM CsCl, 2 mM $MgCl_2$, 10 mM Tris-HCl, pH 8.7) (FIG. 9). To ensure that G3T-ds15 [SEQ. ID. NO. 10] initially anneals to its complementary strand (as double-helix), the sequences were annealed in the presence of CsCl followed by later KCl addition. ($K^+$ is a quadruplex forming cation, while $Cs^+$ does not support quadruplexes [as described in Kankia, S. I. et al. (2001) *Folding of the thrombin aptamer into a G-quadruplex with Sr(2+): stability, heat, and hydration*, J Am Chem Soc, 123, 10799-10804, incorporated by reference herein in its entirety.]). In QPA, the duplex is formed by annealing a shorter version of 2Ap-G3T [SEQ. ID. NO. 10] (unable to form a quadruplex) to the target sequence with subsequent addition of the missing bases by Taq polymerization. The heating curve (black curve, FIGS. 9 and 11) reveals two separate transitions with midpoints at 60° C. and ~95° C.

The transition at 60° C. corresponds to duplex unfolding, which is accompanied by an increase in fluorescence due to quadruplex formation of released G3T-ss15 [SEQ. ID. NO. 10]. The second transition at ~95° C. corresponds to the melting of the quadruplex accompanied by fluorescence quenching of 2Ap due to stacking interactions of adjacent guanines in unstructured 2Ap-G3T [SEQ. ID. NO. 10]. The second transition is completely reversible during the cooling process (-□- in FIGS. 9 and 11). However, no duplex refolding was observed, which clearly indicates that the quadruplex stays folded at lower temperatures in the presence of the complementary strand. In separate isothermal experiments at 40° C., the complementary strand was added to a preformed G3T-ss15 quadruplex [SEQ. ID. NO. 10], which didn't affect the fluorescence spectrum of the quadruplex (data not shown). Thus, both melting and isothermal mixing experiments show that the quadruplex is very stable and the complementary strand is unable to invade the structure. Taken together, these data indicate that G3T primers can potentially inhibit product DNA re-annealing at target sites.

Figure 10:
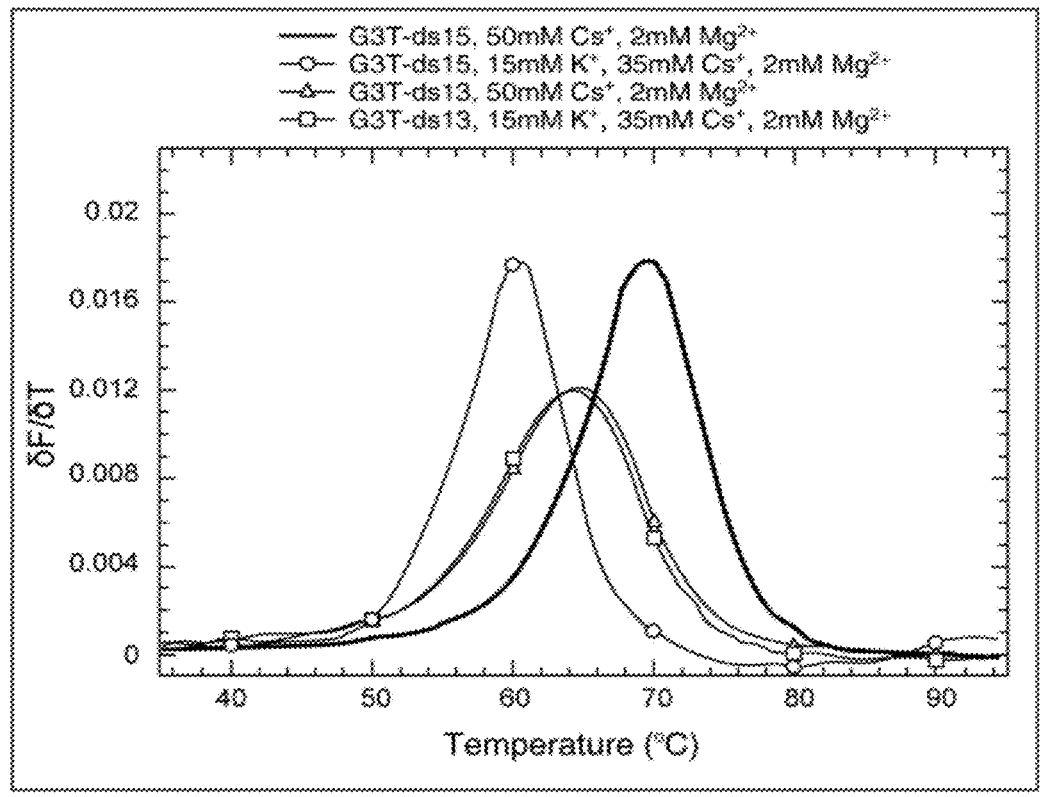
FIG. 10 shows UV melting curves of G3T-ds15 [SEQ. ID. NO. 10] and G3T-ds13 (i.e., GGG(2Ap)GGGTGGGTG [SEQ. ID. NO. 12] in duplex form with a complementary strand CCCTCCCACCCACCC [SEQ. ID. NO. 3]) duplexes in the presence (-o- and -☐-) and absence (-Δ- and black line) of K+ ions.

It is noted that the duplex melting temperature (~60° C.) measured in the presence of the quadruplex forming cation KCl (FIGS. 9 and 11) is significantly lower than the $T_M$=70° C. of the same duplex measured under experimental conditions unfavorable for quadruplex formation (50 mM CsCl and 2 mM $MgCl_2$), or predicted from nearest-neighbor analysis of equilibrium unfolding [Zuker, M. (2003) *Mfold web server for nucleic acid folding and hybridization prediction*, Nucleic acids research, 31, 3406-3415]. To compare thermal stabilities of the G3T-ds15 [SEQ. ID. NO. 10] duplex in the presence and absence of $K^+$, UV absorption was employed (FIG. 10). In the presence of $K^+$ ions G3T-ds15 [SEQ. ID. NO. 10] unfolds at 60° C. (-○-), which is in excellent agreement with results of the fluorescence measurements shown in FIG. 9. In the absence of $K^+$ ions the duplex is significantly more stable and unfolds at 70° C. (-□-) as predicted from nearest-neighbor analysis of equilibrium unfolding [Zuker, M. (2003) *Mfold web server for nucleic acid folding and hybridization prediction*, Nucleic acids research, 31, 3406-3415]. Note an additional small peak at 93° C. in the presence of $K^+$, which corresponds to quadruplex unfolding and again agrees with fluorescence measurements shown in FIG. 9. Additional melting experiments of the G3T-ds15 [SEQ. ID. NO. 10] duplex in the presence of $K^+$ performed at slower heating rates (0.5° C./min and 0.1° C./min) further shifted the transition to lower temperatures (data not shown). Thus, in the presence of $K^+$, unfolding of the duplex is a non-equilibrium process due to quadruplex formation of the released strands, which significantly destabilizes the duplex. FIG. 10 also demonstrates unfolding of G3T-ds13 [SEQ. ID. NO. 12] in the presence and absence of $K^+$ ions, Since G3T-ss13 [SEQ. ID. NO. 12] is not able to form a quadruplex (see FIG. 8), G3T-ds13 [SEQ. ID. NO. 12] duplex melting profiles are identical in the presence and absence of $K^+$ ions with $T_M$=65° C. As expected, in the presence of $Cs^+$ ions the longer duplex, G3T-ds15 [SEQ. ID. NO. 10], is more stable than the shorter duplex, G3T-ds13 [SEQ. ID. NO. 12]. However, in the presence of $K^+$ the opposite is true: the shorter duplex is ~5° C. more stable than the longer one. This result illustrates the potential for isothermal QPA; at appropriate temperatures, the primer is more stable before elongation, which facilitates primer dissociation and the next priming round without the need for thermal denaturation.

Optical and Thermodynamic Properties of the Primers.

Figure 12:
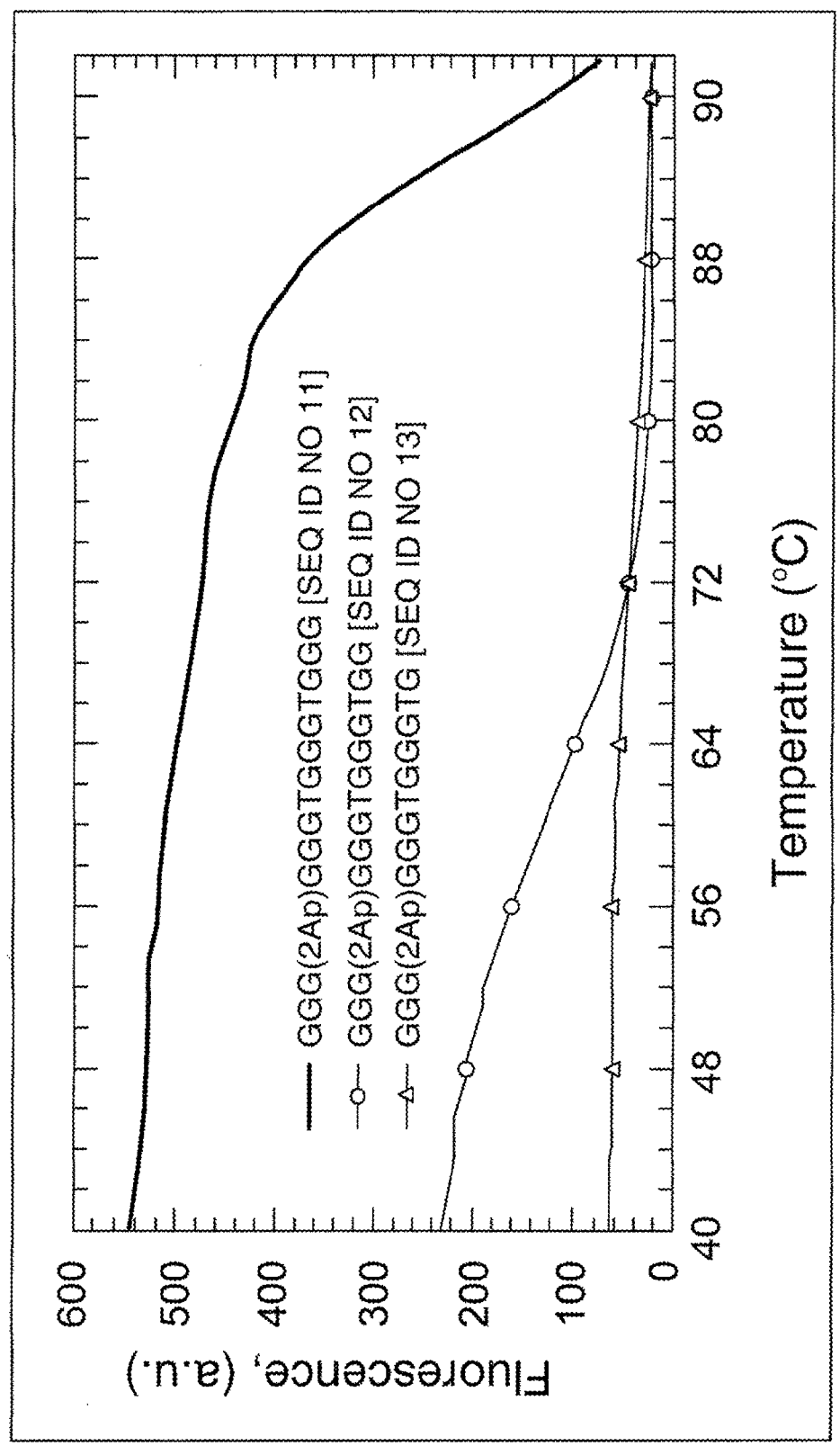
FIG. 12 shows fluorescence melting curves of 2Ap-G3T [SEQ. ID. NO. 10] (black line) and its truncated versions [i.e., G3T-ss14 [SEQ. ID. NO. 11] (-o-) and G3T-ss13 [SEQ. ID. NO. 12] (-Δ-)] in 50 mM KCl.

As mentioned earlier, QPA primers, which in this Example 1 are truncated versions of G3T, should bind target sequences and form duplexes. Referring to FIG. 12, deletion of a single guanine at the 3'-end of G3T significantly destabilized the quadruplex as expected (-○-), however, it is still able to create some quadruplex structure at lower temperatures. Deletion of another guanine completely inhibits quadruplex formation (-Δ-). Thus, the 13-base long GGG(2Ap)GGGTGGGTG [SEQ. ID. NO. 12] sequence fully meets primer requirements as: (i) it binds to the target sequence; (ii) upon addition of two bases it can fold into a quadruplex, and (iii) quadruplex formation is accompanied by a strong increase in 2Ap fluorescence.

QPA Under Isothermal Conditions.

As described above, since the quadruplex is more stable than its corresponding duplex, unfolding of the duplex can proceed without the need for temperature change. To demonstrate this potential of isothermal QPA, and referring now to FIG. 13, a chemically synthesized 51-base long template with an incorporated target site at the 3'-end (bold type) and a quadruplex forming sequence at the 5'-end (bold type) was used. Thus, the template mimics one strand of a DNA amplicon obtained after incorporation of a target site in a DNA template (described in FIG. 5). QPA reactions were performed under experimental conditions (shown in FIG. 11) at 55° C. The experimental temperature was predetermined by the $T_m$ of the primer-target duplex, which is 62° C. The level of fluorescence signal achieved at the plateau region corresponds to 0.8-1 µM quadruplex, which indicates that most of the primers were used in the elongation reactions.

Summary of Data Obtained from Example 1.

Example 1 demonstrates that 2Ap incorporated and quenched within the G3T sequence regains its maximum emission upon quadruplex formation. The fluorescence is comparable to the level of free 2Ap base and sensitive enough to monitor DNA amplification in real-time. Since 2Ap is an intrinsic part of the primers, QPA offers a very simple, inexpensive and truly single-molecular primer/probe system with high sensitivity. Thus, QPA has the potential to overcome most of the shortcomings of current quantitative PCR-based detection mechanisms. The G3T-quadruplex stays folded in the presence of the complementary strand. As a result, the 5'-end of each product DNA is trapped in a quadruplex and its complementary sequence (target) is fully accessible to the next round of primers. Thus, QPA has the potential to liberate traditional PCR from problems associated with product self-annealing, and improve its efficiency. Example 1 also demonstrates that QPA can proceed spontaneously under substantially isothermal conditions.

EXAMPLE 2

Figure 14:
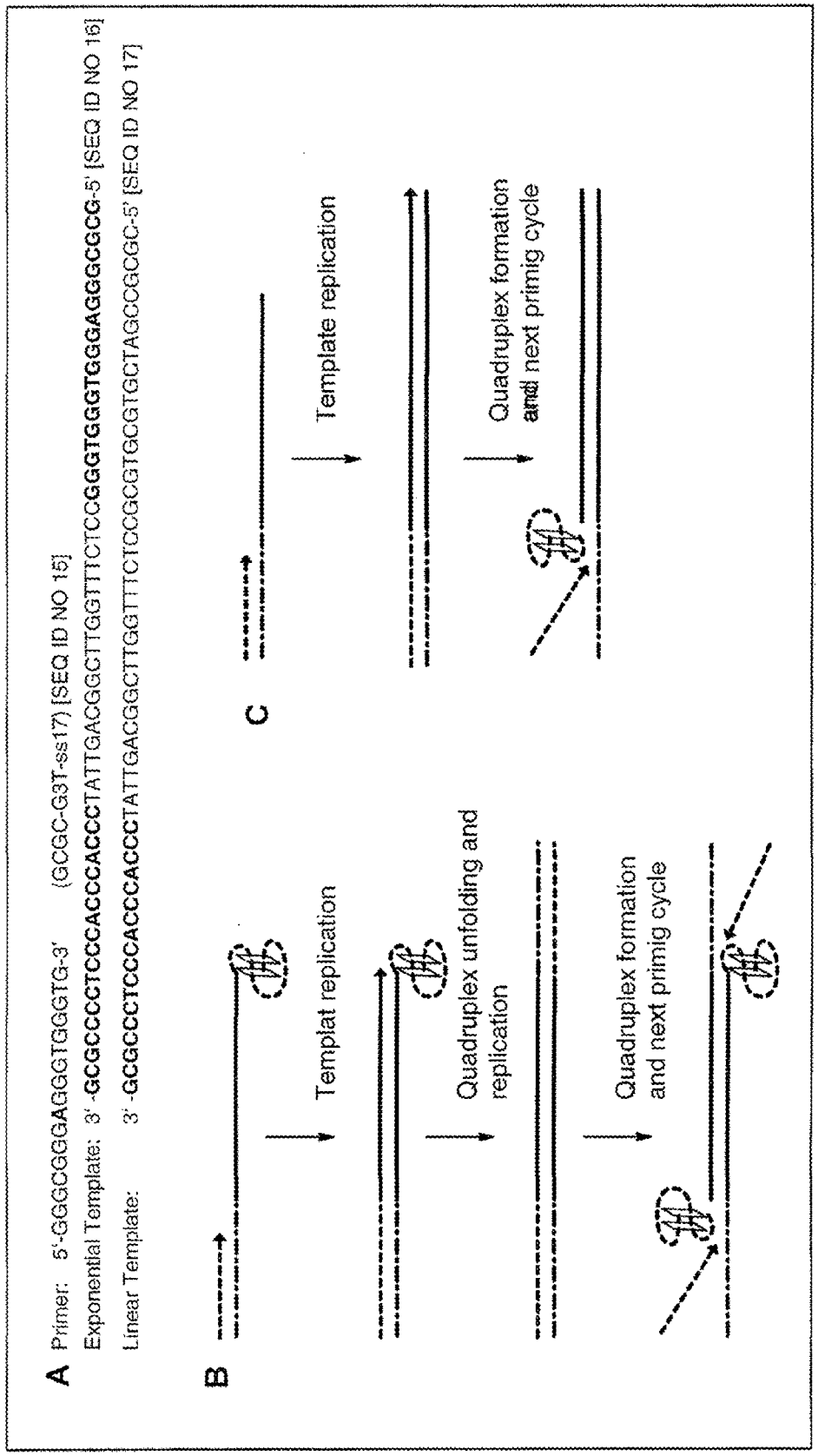
FIG. 14 includes schematics showing the sequence of QPA primer and templates used in the reactions (panel A), exponential QPA (in panel B), and linear QPA (in panel C).

To further demonstrate the potential of isothermal QPA, two similar templates with incorporated primer binding sites (PBS) (bold type segments at 3'-end in FIG. 14, panel A) were used. The "exponential" template contains a quadruplex forming sequence at the 5'-end (bold type segment at 5' end in FIG. 14, panel A), which is fully complementary to 19-base PBS and allows incorporation of the PBS to newly generated amplicons (FIG. 14, panel B). The amplicons are used as templates in the following rounds of replication, setting up an exponential amplification pattern. In the "linear" template, the quadruplex forming sequence is scrambled. As a result, Taq is able to replicate only the initial templates, setting up a linear amplification pattern (FIG. 14, panel C).

Further, the primer having a GCGC sequence at the 5'-end, which increases the thermal stability of primer-target complex to 76° C. and allows isothermal QPA to be performed at optimal temperatures for enzymatic activity of Taq (70-75° C.). To ensure that the attachment of GCGC does not affect the quadruplex forming ability of G3T-ss15 [SEQ. ID. NO. 10], additional studies were performed (data not shown), and no significant effects of GCGC-attachment was observed. Additionally, in the exponential template, PBS and quadruplex-forming segments are fully complementary to each other with a possibility of forming a stem, thus inhibiting primer binding. However, in the presence of $K^+$ ions, the quadruplex sequence folds into a quadruplex and the PBS is accessible for primers, as shown schematically in FIG. 14B.

Experiments at 100 nM Template.

Experiments have been designed to demonstrate the isothermal nature of QPA at rather high concentrations of template (100 nM). The addition of Taq polymerase into reaction mixtures initiated rapid fluorescence emission (FIG. 15), which is attributed to quadruplex formation upon polymerase elongation. Results of these experiments reveal three major features of QPA: (i) amplification is isothermal without any input of additional factors or enzymes; (ii) DNA yield appears to be unusually high and reaches the initial concentration of primers, 1 µM (traditional PCR usually plateaus at low nanomolar concentrations); and (iii) amplification can be monitored by intrinsic fluorescence of primers containing 2Ap. To confirm that the fluorescence increase in FIG. 15A corresponds only to quadruplex formation, negative controls in the absence of (i) quadruplex forming cations, (ii) Taq, and (iii) templates were performed, which did not reveal any fluorescence increase (data not shown).

Figure 15A:
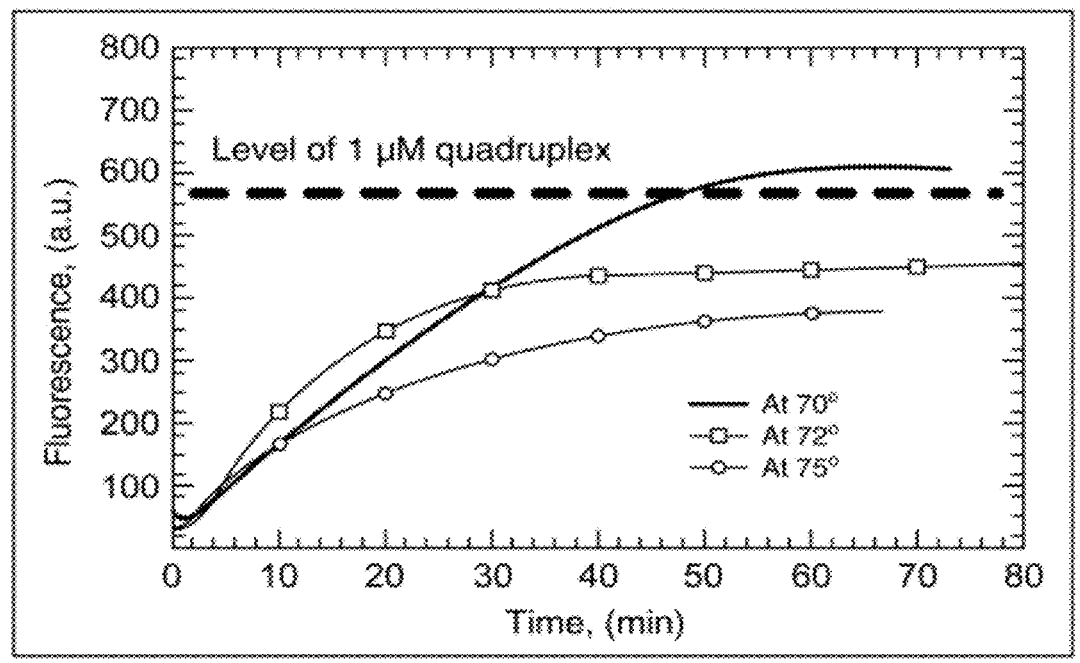
FIG. 15A shows isothermal QPA using 100 nM template, 1 µM primer, 200 µM dNTPs and 5 U Taq in 100 µL buffer (25 mM KCl, 25 mM CsCl, 2 mM MgCl$_2$).

As shown in FIG. 15A, increasing reaction temperature results in QPA rate enhancement, however, at higher temperatures product yield declines. For instance, at 70° C. QPA reaches 100% yield at ~50 min, while at 72° C. the reaction levels off at ~30 min with 80% yield. The role of temperature is not clear from the preliminary experiments, since QPA includes several steps (priming, elongation and dissociation of elongated primer from PBS). Each of these processes strongly depends on the temperature as well as the ionic strength. Thus, the role of temperature and ionic strength to find out the most favorable conditions for QPA will be studied.

Figure 15B:
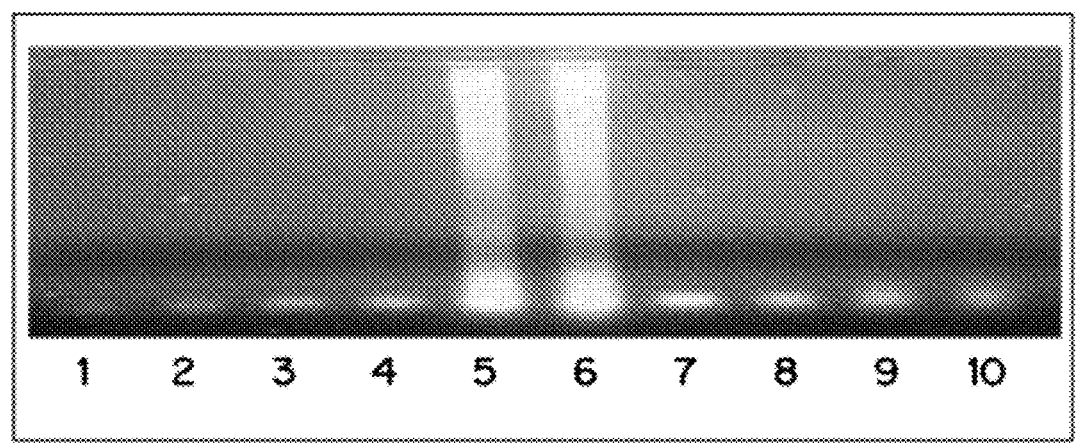
FIG. 15B is a photograph of agarose gel electrophoresis of the QPA products shown in FIG. 15A visualized by ethidium bromide, where lanes 2 and 3 are product at 75° C., lanes 3 and 4 are product at 72° C., lanes 5 and 6 are product at 70° C. after 10 hours of kinetics, lanes 7 and 8 are product at 70° C. after 70 min of kinetics, and lanes 9 and 10 are 1 µM positive control (a chemically synthesized product duplex).

Comparison of the fluorescence results in FIG. 15A with gel electrophoresis of QPA products in FIG. 15B also reveals that QPA detection is superior at monitoring amplification of specific products only. Lanes 5 and 6 correspond to products formed at 70 min and after overnight reaction (10 h), respectively. Note that the overnight incubation produced higher molecular weight DNA, which is likely the result of Taq enzymatic activity after consuming the primers. However the non-specific DNA, which is detected by electrophoresis is undetectable by fluorescence measurements (plateau level stays the same during the overnight reaction, data not shown). The high accuracy of QPA, or sensitivity to only specific products, can be explained by the fact that its specificity is not only determined by target binding, but also by proper elongation of the next few bases to create a quadruplex. For instance, the QPA described in FIG. 15A requires two cytidines (underlined in FIG. 14A) adjacent to the PBS. It is known that quadruplexes do not tolerate nucleotide substitutions in their G-tracts [Kankia, B. I. (2004) *Optical absorption assay for strand-exchange reactions in unlabeled nucleic acids*, Nucleic acids research, 32, p. 154; Smirnov, I. and Shafer, R. H. (2000) *Effect of loop sequence and size on DNA aptamer stability*, Biochemistry, 39, 1462-1468]. Thus, nonspecific priming alone is not sufficient to form a quadruplex and produce a false signal. In addition, the non-specifically bound primer would have to bind at cytidine tracts, which further decreases the probability of a false signal.

Experiments at Low Concentrations of Templates.

Figure 16A:
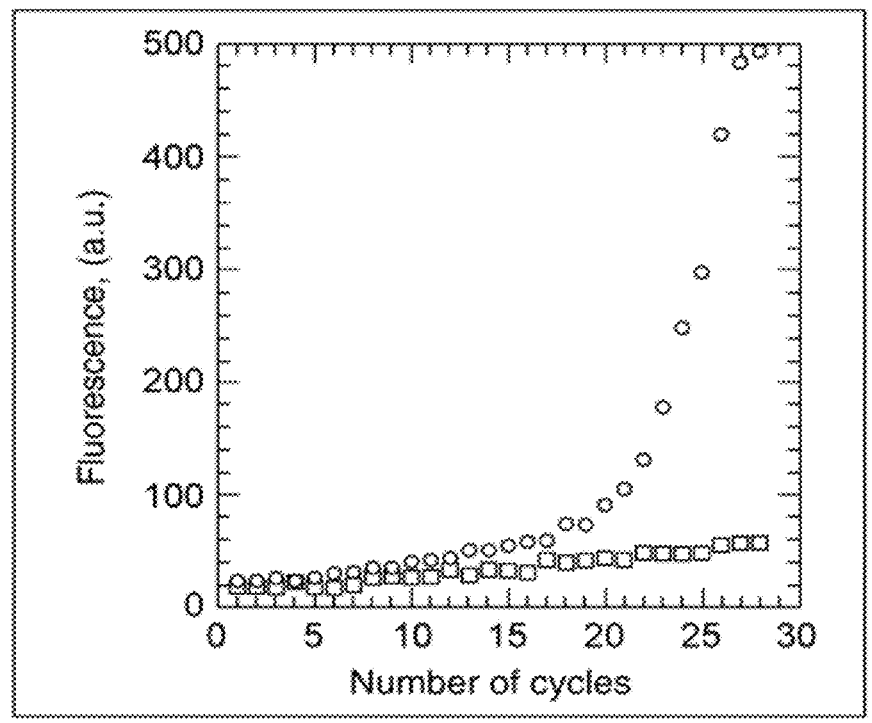
FIG. 16A is a graph showing thermo-cycling QPA of exponential (circles) and linear (squares) templates at 70° C. for 3 min and 94° C. for 1 min, where the reaction mixtures (100 µl) include 1 µM primer, 200 µM dNTPs, 5 U Taq, 5 mM KCl, 45 mM CsCl, 2 mM MgCl$_2$, 10 mM Tris-HCl at 10 fM template.
Figure 16B:
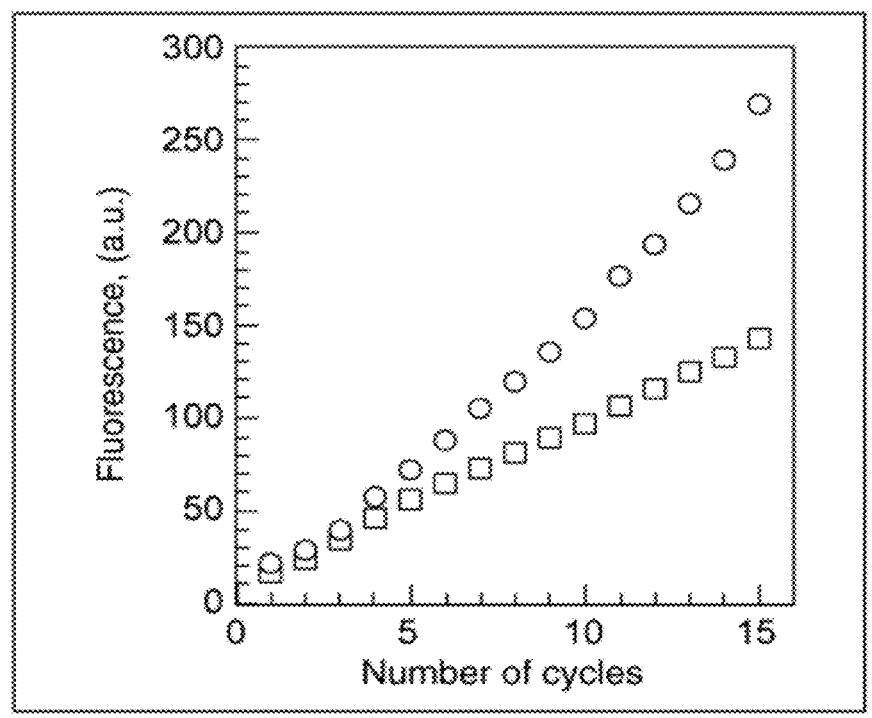
FIG. 16B is a graph showing thermo-cycling QPA of exponential (circles) and linear (squares) templates at 70° C. for 3 min and 94° C. for 1 min, where the reaction mixtures (100 µl) include 1 µM primer, 200 µM dNTPs, 5 U Taq, 5 mM KCl, 45 mM CsCl, 2 mM MgCl$_2$, 10 mM Tris-HCl at 1 nM template.

The experiments shown in FIG. 15, were performed under experimental conditions where Taq is the limiting reagent. Thus, they do not reveal the amplification potential (exponential or linear) of QPA. In order to perform exponential amplification, Taq polymerase must replicate the entire template including the quadruplex (FIG. 14). To do so, Taq must unfold the G3T-ss15 [SEQ. ID. NO. 10] quadruplex upon polymerization, which may be impeded by the high stability of the quadruplex. Thus, high concentrations of $K^+$ can have both positive (accelerate QPA through faster primer-PBS dissociation) and negative effects (limit QPA to only linear amplification). Thus, optimizing $K^+$ concentration will be a critical first step to find optimal conditions for exponential amplification by QPA. In a preliminary study, both processes were favored (primer-PBS dissociation and quadruplex unfolding/replication by Taq) by performing thermo-cycling QPA at low concentrations of $K^+$ ions (5 mM). Typical thermo-cycling QPA reactions conducted at 10 fM template are shown in FIG. 16A. In the presence of the exponential template (see FIG. 14A), clear exponential increase of the fluorescence signal after the 17th cycle was observed. QPA points from 17 to 26 in FIG. 16A were fit to the exponential expression to obtain the slope, and to calculate the efficiency (E) of QPA, $E=e^{slope}=e^{0.62525}=1.87$ (E=2 corresponds to 100% efficiency). As expected, QPA using a linear template does not show any significant fluorescence increase (squares, FIG. 16A). To detect measurable effects for both exponential and linear amplification under the same conditions, similar experiments were performed in the presence of 1 nM templates (FIG. 16B). In this reaction, Taq concentration becomes limiting after a few cycles, however, the difference between linear and exponential amplification is still obvious.

Figure 17A:
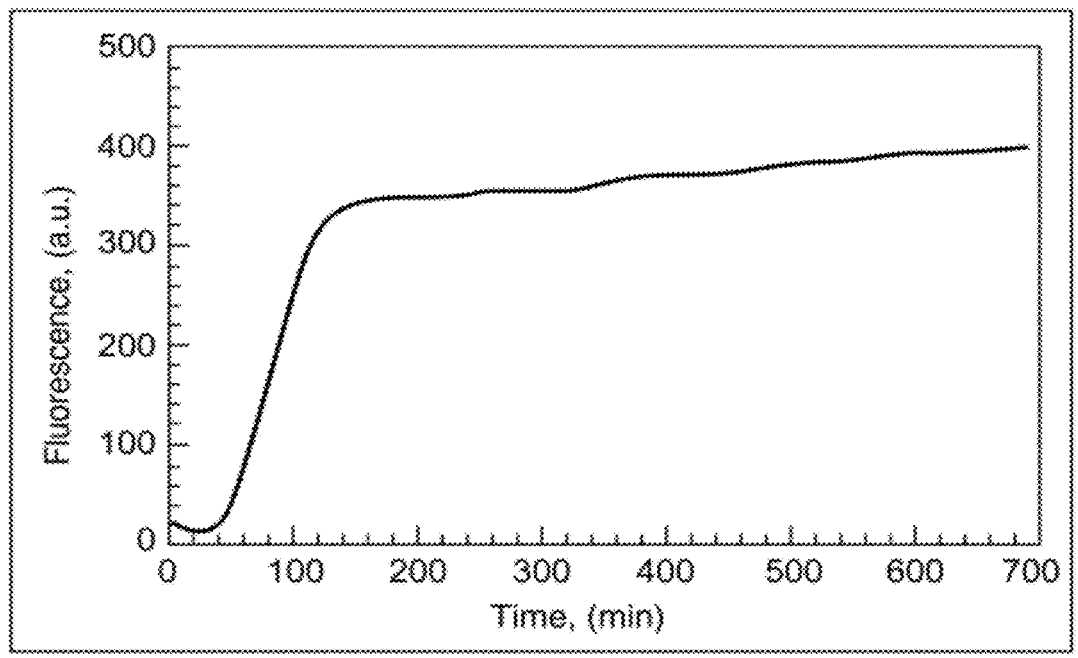
FIG. 17A is a graph showing isothermal QPA at 72° C. using 10 µM template, 1 µM primer, 200 µM dNTPs and 5 U Taq in 100 µL buffer (25 mM KCl, 25 mM CsCl, 2 mM MgCl$_2$).
Figure 17B:
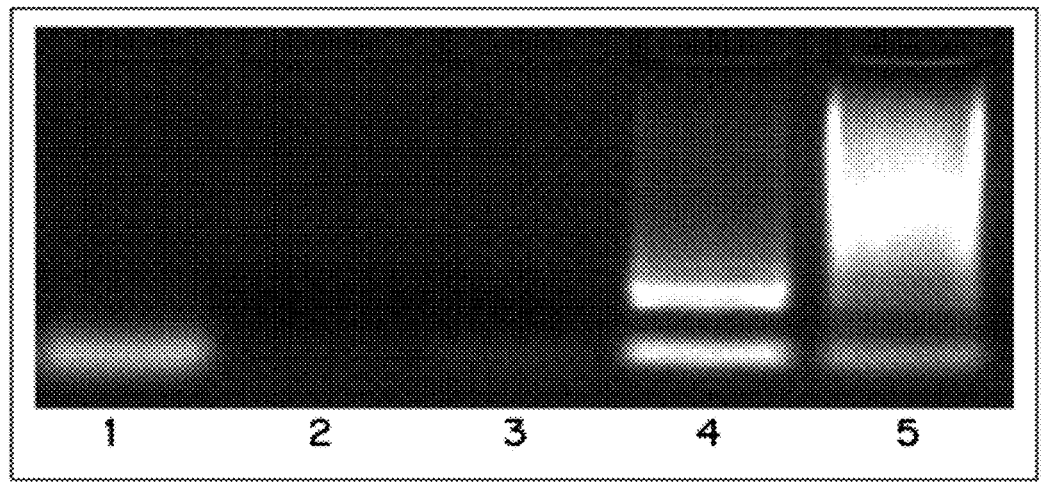
FIG. 17B is a photograph of agarose gel electrophoresis of QPA products shown in FIG. 17A visualized by ethidium bromide, where lane 1 is chemically synthesized product duplex, lane 2 is product at 30 min, lane 3 is product at 80 min, lane 4 is product at 200 min, and lane 5 is product at 700 min.

To reveal the exponential nature of QPA under isothermal conditions, different experimental conditions were tested, and good activity was observed using 10 μM template in the presence of 25 mM KCl at 72° C. (FIG. 17A). The fluorescence signal increases after 40 min and at ~100 min reaches a plateau corresponding to ~0.8 μM single-stranded product. The reaction was allowed to proceed for another 10 hours, and during this time the fluorescence signal remained at the plateau level. Product formation was also followed by agarose gel electrophoresis (FIG. 17B). These results demonstrate that non-specific DNA starts to accumulate after the plateau is reached. This product does not have any significant effect on the fluorescence signal (FIG. 17A), most likely because it does not involve the quadruplex forming sequence used to detect the desired product. Thus, this experiment confirms that QPA detection is sensitive to only the specific product even in the presence of significant amounts of non-specific DNA.

Incorporation of QPA Primer Binding Sites into DNA Templates.

Since QPA uses a universal primer, the PBS must be incorporated into a target template. This can readily be accomplished by only two cycles of traditional PCR in which the 5'-end of both forward and reverse primers have quadruplex attachments (FIG. 5). Note that here the quadruplex attachments are used only for PBS incorporation, and not for 2Ap-based detection. The product of the 2nd PCR cycle contains two amplicons with incorporated target sites at the 3'-end (FIG. 5, dashed lines). Thus, at the end of the 2nd cycle, the number of amplicons with incorporated QPA target sites equals the initial amount of template, which is important for accurate DNA quantification. QPA will amplify only these two desired templates, and not the other six unwanted templates, which are usually amplified in traditional PCR.

Figure 18:
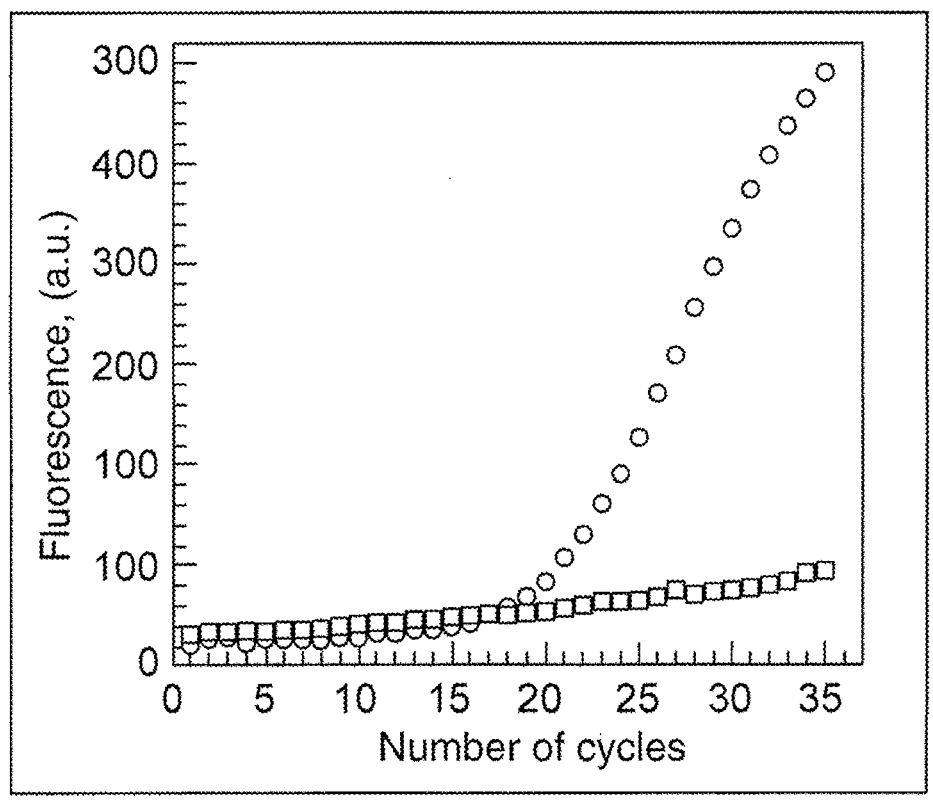
FIG. 18 shows thermocycling QPA after attachment of QPA-target sites to a pUC18 cloning region (101-nt), and where the negative control (squares) does not include initial PCR primers.

FIG. 18 demonstrates successful QPA target site incorporation into a pUC18 cloning region using the sequencing primers (forward primer, GTAAAACGACGGCCAGT [SEQ. ID. NO. 4], $T_M$ of 64° C.; reverse primer, GGAAACAGCTATGACCA [SEQ. ID. NO. 5], $T_M$ of 59° C.) with an attached quadruplex-forming sequence (GCGC-G3T-ss15) [SEQ. ID. NO. 22]. Initial two cycles of traditional PCR were conducted at three different temperatures (53° C., 72° C. and 94° C. for 30 s each). Then, the QPA-primer was added and RT-QPA was performed by cycling between two temperatures as follows: 72° C. for 60 s and 94° C. for 12 s, which demonstrates exponential amplification (FIG. 18). Note that 72° C. is too high for the sequencing primers and their priming is negligible during QPA. As expected, the negative control (no initial sequencing primers) shows no amplification (squares, FIG. 18). While a few temperature changes can be easily performed in a laboratory without a thermocycler, truly isothermal systems are desirable for Global Health diagnostics. However, even semi-isothermal QPA described in FIGS. 5 and 18 will be a very useful addition to any PCR-based detection platforms, since its high yield will allow thorough multi-well diagnostics.

EXAMPLE 3

Figure 19:
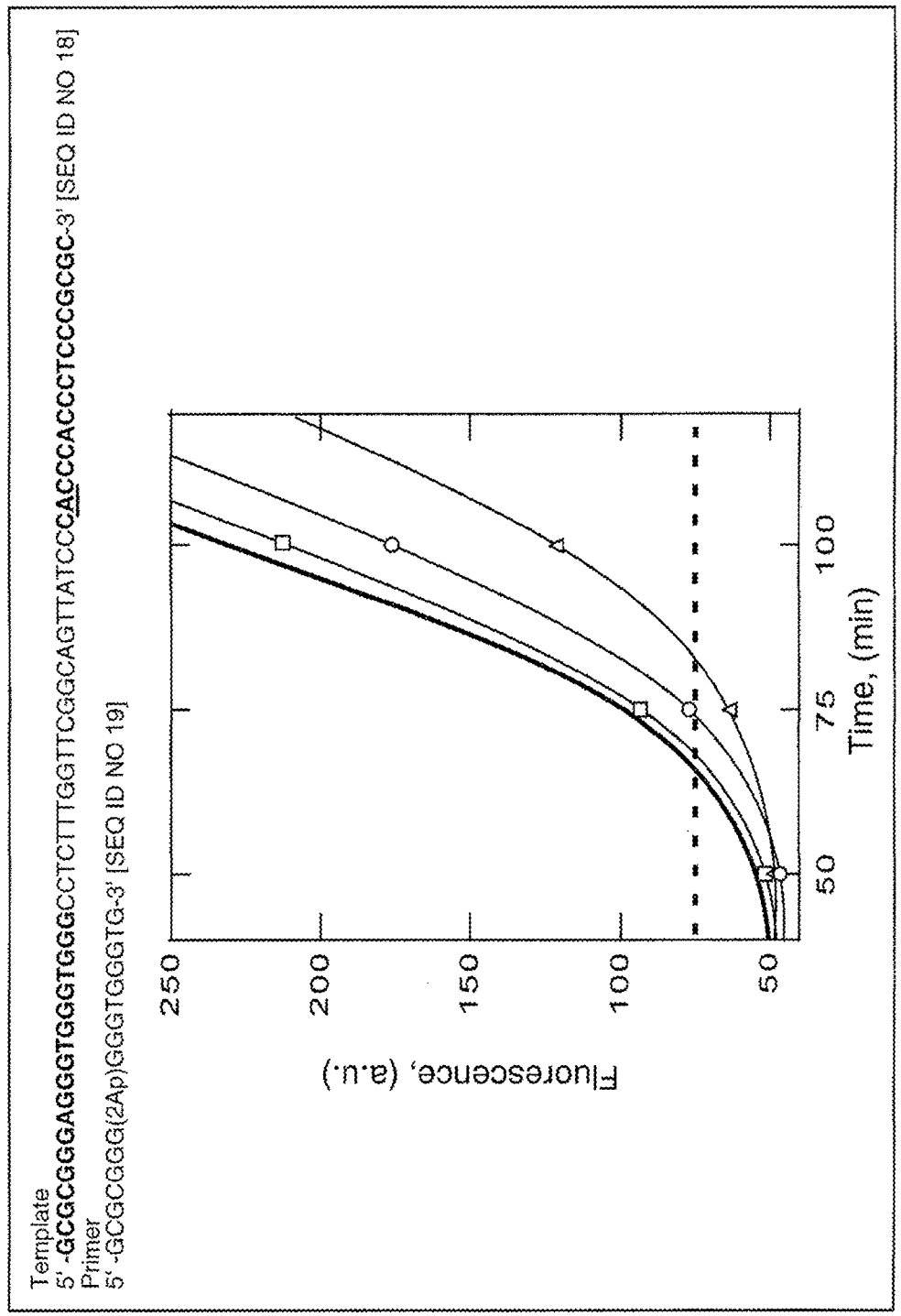
FIG. 19 shows isothermal RT-QPA at 72° C. using the shown template and target with a reaction mixture (100 µl): 1 µM primer, 20 µM dNTPs, 5 U Taq, 50 mM KCl, 2 mM MgCl$_2$, 20 mM Tris-HCl, pH 8.7 at 50 fM (-Δ-), 1 µM (-○-), 5 µM (-□-), and 10 µM (black line) template DNA.

To further demonstrate the potential of QPA, a chemically synthesized 59 base long template with an incorporated target site at the 3' end (FIG. 19, -○-) and a quadruplex-forming sequence at the 5' end (FIG. 19, -Δ-) was used. This template mimics one strand of a DNA amplicon obtained after incorporation of a target site in a DNA template (as described previously, and as shown schematically in FIG. 5). The primer has the GCGC sequence attachment at its 5' end, which increases its $T_m$ to 76° C. [as described in Zuker, M. Mfold web server for nucleic acid folding and hybridization prediction, *Nucleic Acids*, 31, pp. 3406-3415 (2003)], and allows isothermal QPA to be performed at optimal temperatures for Taq activity (70-75° C.). QPA was successfully performed under isothermal conditions.

EXAMPLE 4

Example 4 is a prophetic example for the optimization of QPA. In particular, Example 4 will investigate efficiency of QPA at varying concentrations of KCl, primers, dNTPs and Taq polymerase. These studies will define optimal conditions for QPA and for incorporation of QPA target sites into templates. It is expected that QPA will increase the exponential growth phase and increase DNA yield, thereby improving the efficiency of PCR.

Optimizing Experimental Conditions for QPA.

$K^+$ is a quadruplex folding cation [Kankia, B. I. et al. (2001) Folding of the thrombin aptamer into a G-quadruplex with Sr(2+): stability, heat, and hydration. *J Am Chem Soc*, 123, 10799-10804] and therefore it is an essential component of QPA (see FIG. 2). Increasing K+ concentration will facilitate quadruplex formation and may accelerate QPA. This is due to the fact that the stability of the G3T quadruplex is proportional to the K+ concentration. However, high concentrations of K+ can have negative effects on QPA efficiency. Specifically, in order to perform exponential amplification, Taq polymerase should replicate the entire template including the G3T quadruplex (see FIG. 5). To do so, Taq must unfold the G3T quadruplex upon polymerization, which may be impeded by the high stability of the quadruplex. Thus, high concentrations of K+ can have both positive (accelerate QPA) and negative effects (limit QPA to only linear amplification). Therefore, it will be important to optimize the concentration of K+ to achieve maximal QPA efficiency and the longest exponential growth step.

Thus, RT-QPA will be performed at different concentrations of K+, while maintaining an ionic strength of 50 mM by adding appropriate amounts of CsCl. Cs+ does not support quadruplex formation and acts as a non-specific cation to stabilize primer-target duplexes. Chemically synthesized templates (similar to those shown in FIG. 13), will be used, with the target sites corresponding to the most efficient primers, as will be discussed below in Example 5.

In these reactions, QPA will be performed at femtomolar or picomolar concentrations of the template. It is expected that exponential amplification will result in an exponential increase in the fluorescence signal. (At high concentrations of template a potential limiting factor could be the amount of Taq rather than template concentration). As a negative control, a similar template without a quadruplex forming sequence at the 5'-end will be used.

In these reactions, newly produced DNA will be missing target sites and Taq can use only initial templates for amplification and one should observe a linear increase in fluorescence measurements. Standard experimental conditions for successful PCR typically include 0.1-1 µM primers, 200 µM dNTPs and 1-5 Units of Taq. Since in QPA primer dimerization is excluded (QPA uses a single primer), complications at higher primer concentrations (i.e. 2-5 µM) are not expected. In addition, QPA has the potential to elongate the exponential part of traditional PCR, and therefore increase the number of cycles corresponding to the plateau region. Thus, testing QPA at varying concentrations of primers, dNTPs and Taq polymerase will be performed to find the most efficient conditions.

If exponential growth at any concentration of K+, which means that Taq was unable to invade stable K-quadruplexes, fails to occur, other cations known to form less stable quadruplexes (i.e. Rb+, NH4+, Na+ or Ba2+) will be tested [Kankia, B. I. et al. (2001) Folding of the thrombin aptamer into a G-quadruplex with Sr(2+): stability, heat, and hydration. *J Am Chem Soc*, 123, 10799-10804].

Validating QPA as a More Efficient Amplification Method.

Incorporation of target sites into a DNA template will initially be demonstrated on the commonly used pUC18 plasmid vector. To amplify the 103-bp long multiple cloning site, the following standard 17-mer sequencing primers will be used: forward primer, GTAAAACGACGGCCAGT [SEQ. ID. NO. 4] with a $T_m$ of 64° C. and reverse primer, CAGGAAACAGCTATGAC [SEQ. ID. NO. 6], with a $T_m$ of 58° C. in 50 mM monovalent cation and 2 mM MgCl$_2$. The quadruplex forming sequence (i.e., 5'-CGGCGGGAGGGTGGGTGGG-3') [SEQ. ID. NO. 7] will be attached at the 5'-end of each primer.

Since only two cycles of traditional PCR are needed, combined 34-mer primers will be used at relatively low concentrations (10-50 nM). The PCR will be performed at three different temperatures: 53° C. (priming), 72° C. (elongation) and 94° C. (unfolding). After two cycles, the amount of DNA amplicons with incorporated target sites (5'-CCCACCCACCCTCCCGCCG-3') [SEQ. ID. NO. 8] will be equal to the initial number of DNA templates (see FIG. 5) and amplification will be continued by QPA at 72° C. after adding 1 µM QPA primer (5'-CGGCGGG(2Ap)GGGTGGGTG-3' [SEQ. ID. NO. 23] with $T_m$ of ~76° C.). Further, this temperature is too high for the initial 34-mer primers and therefore their priming will be completely excluded. As a negative control, the same reaction without initial primers will be performed.

Following the initial 2 cycles of PCR to incorporate the target sites, QPA vs. traditional PCR amplification strategies will be compared. Reactions will be performed using the same sequencing primers with and without quadruplex attachments. The amount of DNA in both systems (QPA with 34-mer primers and PCR with 17-mer primers) following 30-40 rounds of amplification will be quantified using a molecular beacon with a 6-bp long stem and 20-nt long loop complementary to the product DNA. The fluorescence will be monitored using an Eclipse spectrophotometer (Varian) with temperature controlled cell holders. Experiments will be performed directly in fluorescence cells, and temperature will be controlled automatically by the Eclipse software, which allows an unlimited number of temperature steps during a single experiment. It is expected that the exponential growth phase for QPA will be longer than for traditional PCR.

Alternative Strategies.

All of these experiments are planned for using standard (multi-use) fluorescence cells. This will increase chances of contamination. Therefore, special care will be taken for cleaning the cells. Specifically, negative controls (no templates) will be routinely performed and appropriate washing procedure will be designed for complete eliminating of DNA products (i.e. using strong detergents, base solutions or other DNA degrading agents).

EXAMPLE 5

Example 5 is a prophetic example for establishing optimal experimental conditions for isothermal QPA. Isothermal QPA will significantly simplify current amplification systems since it does not require expensive instrumentation for thermocycling, or additional enzymes and allows DNA amplification in the field and at point-of-care.

Optimizing Primer Design for Isothermal QPA.

Figure 11:
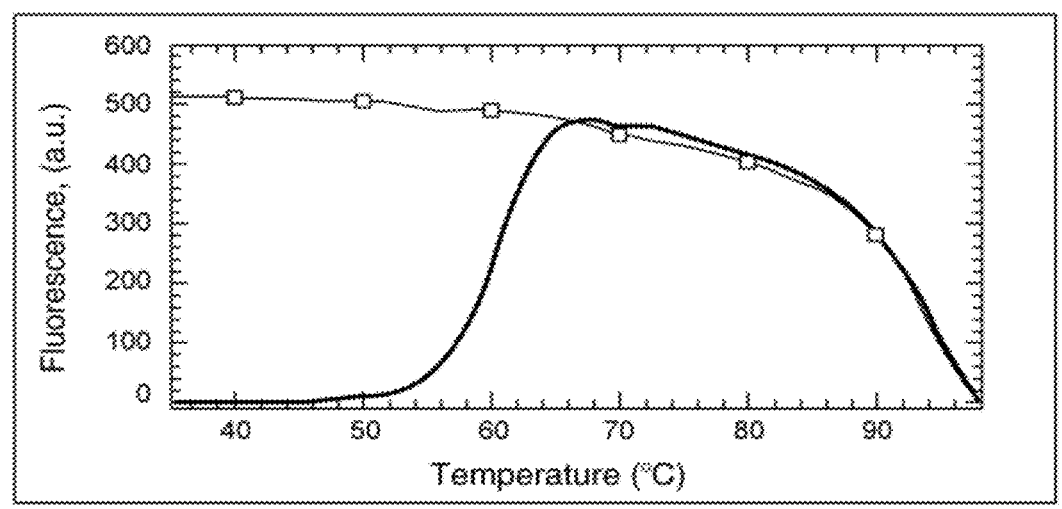
FIG. 11 shows fluorescence melting curves of a 2Ap-G3T [SEQ. ID. NO. 10] duplex in 15 mM KCl, 35 mM CsCl, 2 mM MgCl2, 20 mM Tris-HCl, pH 8.7 wherein the black and squared lines correspond to heating and cooling (at 1° C./min rate), respectively.

In our preliminary studies, a G3T sequence with a $T_m$ of 62° C. in 50 mM monovalent salt and 2 mM MgCl$_2$ was used, which predetermined the rather low elongation step temperature of 55° C. (FIG. 11). As mentioned earlier, the most suitable temperature for isothermal QPA is ~75° C., which corresponds to Taq's optimal activity. In addition, at higher temperatures product duplexes will be more destabilized, which will facilitate the strand-displacement process upon DNA elongation. Therefore, QPA experiments between 70° C. and 85° C. will be performed, and for each temperature new primers with corresponding $T_m$s will be designed. To increase the $T_m$ of the primers, extra nucleotides will be added at the 5'-end of G3T sequence. For instance, the CGGC-GGG(2Ap)GGGTGGGTG (CGGC-G3T) [SEQ. ID. NO. 23] primer demonstrates a $T_m$ of 76° C. [Zuker, M. (2003) Mfold web server for nucleic acid folding and hybridization prediction. Nucleic Acids Res, 31, 3406-3415], which will allow isothermal QPA to be performed at 70-72° C.

Design of Isothermal QPA.

As mentioned above, the tested version of QPA requires temperature changes during the initial two cycles (see FIG. 5), which allows incorporation of QPA-target sites into the templates. While a few temperature changes can be easily performed in a laboratory without a thermocycler, truly isothermal QPA is desirable during detection of pathogenic microorganisms in the field, at check-points or point-of-care. Truly isothermal QPA will be designed, which is based on the fact that QPA-target site incorporation occurs at very low concentration of the DNA templates (femtomolar or low picomolar). At these concentrations the stability of DNA polymers is greatly decreased and they unfold at ~85° C. in the presence of the 50 mM monovalent cations and 2 mM $MgCl_2$ [Zuker, M. (2003) Mfold web server for nucleic acid folding and hybridization prediction. *Nucleic Acids Res*, 31, 3406-3415]. The thermal stability is further decreased to 82° C. in the presence of 10 mM monovalent cations and 1 mM $MgCl_2$. It is hypothesized that by designing initial and universal primers with $T_m$s~82-85° C., one should be able to perform entire QPA under isothermal conditions.

To perform isothermal QPA at 80° C., a primer with a $T_m$ of ~84° C. will be designed, which would require a 7-9 nucleotide attachment to the G3T primer. Thus, the longer primers can potentially fold into dimers. Therefore, particular care will be taken during the primer design, and additional experiments (CD spectroscopy and UV thermal unfolding) will be performed to avoid primer dimerization.

EXAMPLE 6

Example 6 is a prophetic example whereby an ultrasensitive primer-probe will be designed by incorporation several 2Aps in QPA primers. DNA will be quantified as a function of number of cycles (thermocycling QPA) and time (isothermal QPA). These studies will develop a sensitive, robust, simple and universal real-time detection and quantification method which will significantly simplify current techniques.

Primers with Higher Fluorescence Yield.

Figure 7:
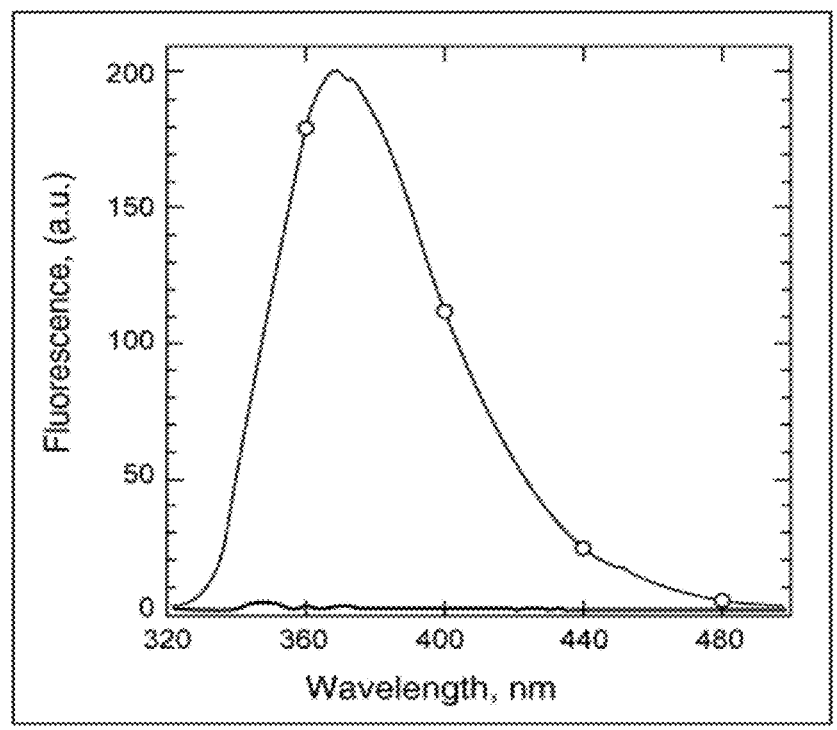
FIG. 7 is fluorescence spectra at 20° C. of 2Ap-G3T [SEQ. ID. NO. 10] in 50 mM KCl in the absence of complement (-o-) and in the presence of the complementary strand in 50 mM CsCl (black line), showing that under the latter conditions, 2Ap-G3T [SEQ. ID. NO. 10] forms a perfect duplex with completely quenched 2Ap.

As shown in the preliminary studies, 2Ap incorporated in the 4th position of G3T gives ~100-fold increase in fluorescence signal upon quadruplex formation (FIG. 7). Specifically, emission of 2Ap incorporated within the folded quadruplex corresponds to emission of the 2Ap free base with a quantum yield of 0.68 [Ward, D. C. et al. (1969) Fluorescence studies of nucleotides and polynucleotides. I. Formycin, 2-aminopurine riboside, 2,6-diaminopurine riboside, and their derivatives. *J Biol Chem*, 244, 1228-1237]. Thus, the fluorescence signal emitted upon QPA is sensitive enough to be used for product detection in RT-PCR. However, even more sensitive probes are proposed by incorporating several 2Aps at loop regions of G3T. The loop region is the most convenient location to avoid quenching from neighboring bases and reach the maximum emission of 2Aps.

Figure 6:
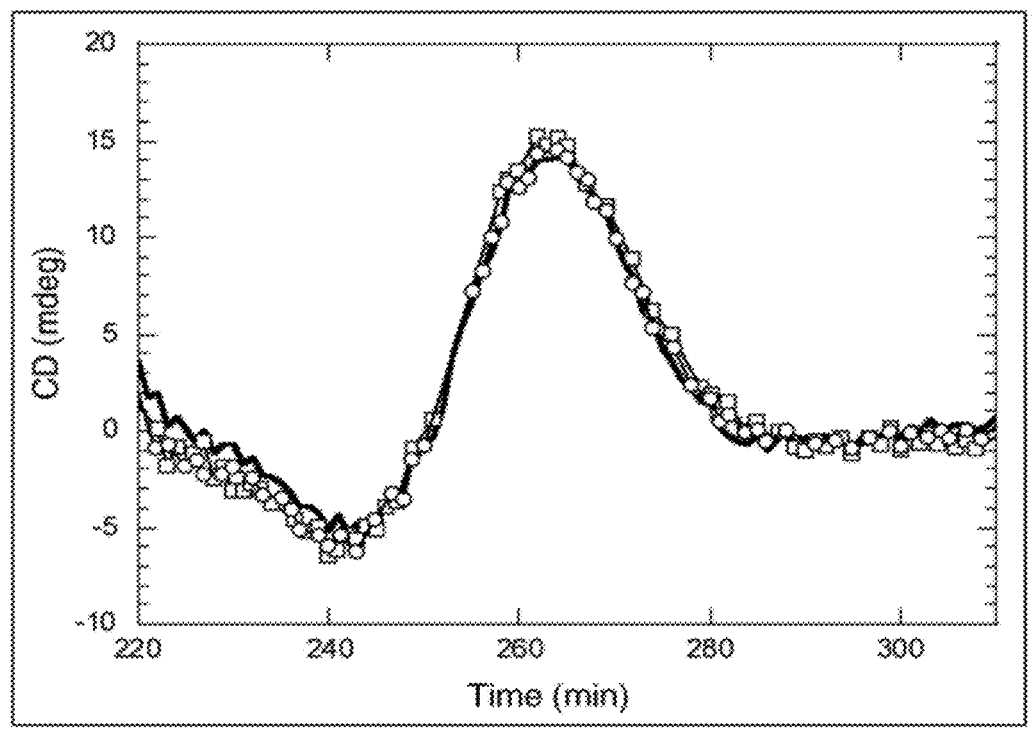
FIG. 6 is a CD spectra of (GGGT)4 (black line), GGGTGGGTGGGTGGG ["(GGGT)3GGG"] (-☐-) [SEQ. ID. NO. 2], and 2Ap-G3T (-o) [SEQ. ID. NO. 10] using 5 µM concentration in 50 mM KCl, 2 mM MgCl2, 20 mM Tris-HCl, pH 8.7 at 20° C.
Figure 20:
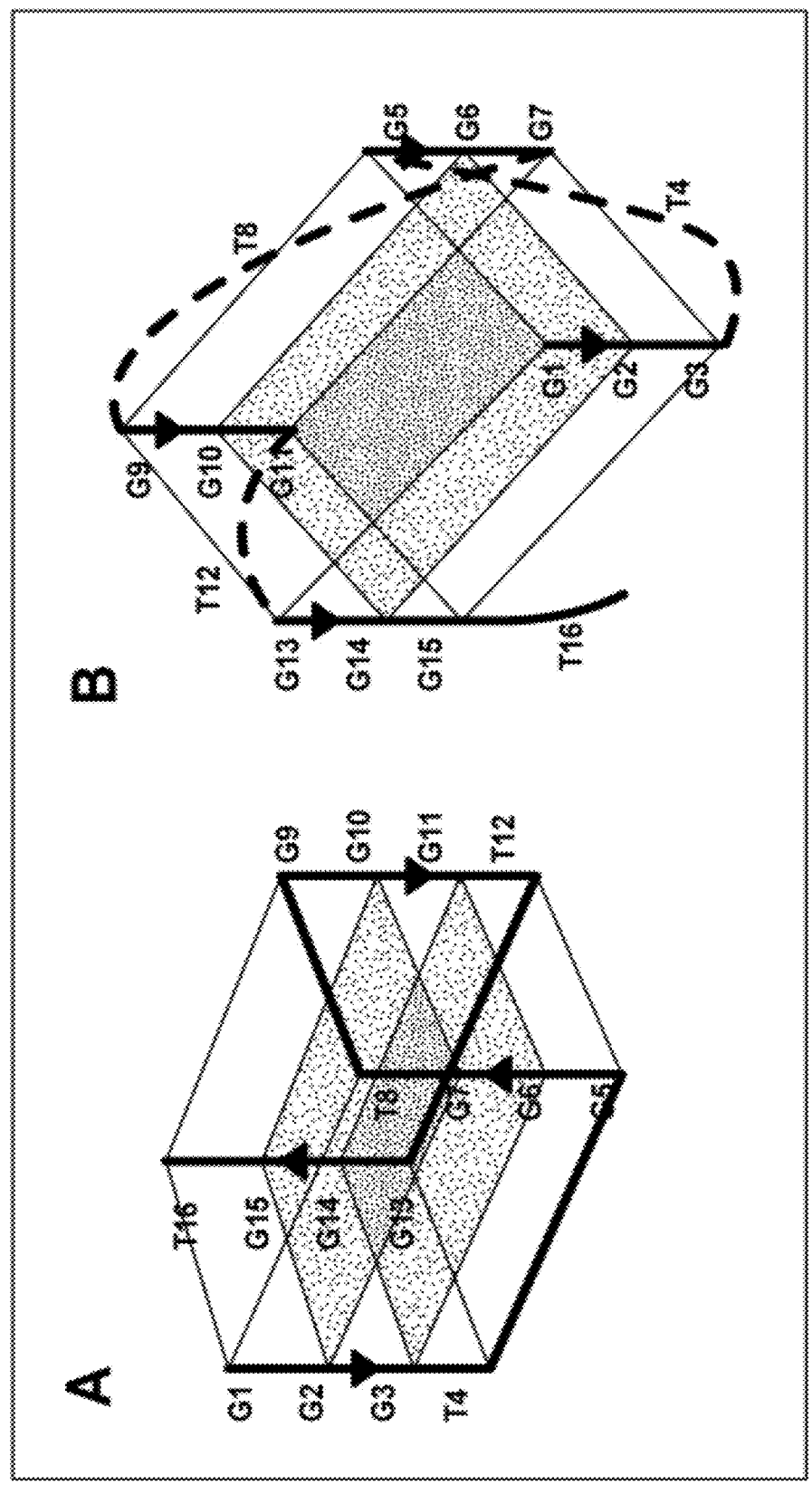
FIG. 20 includes schematic diagrams showing two possible structures of (GGGT)$_4$ [SEQ. ID. NO. 10] with panel A showing an anti-parallel conformation based on NMR work, and with panel B showing a parallel conformation suggested on the bases of thermodynamic and spectral studies.
Figure 21:
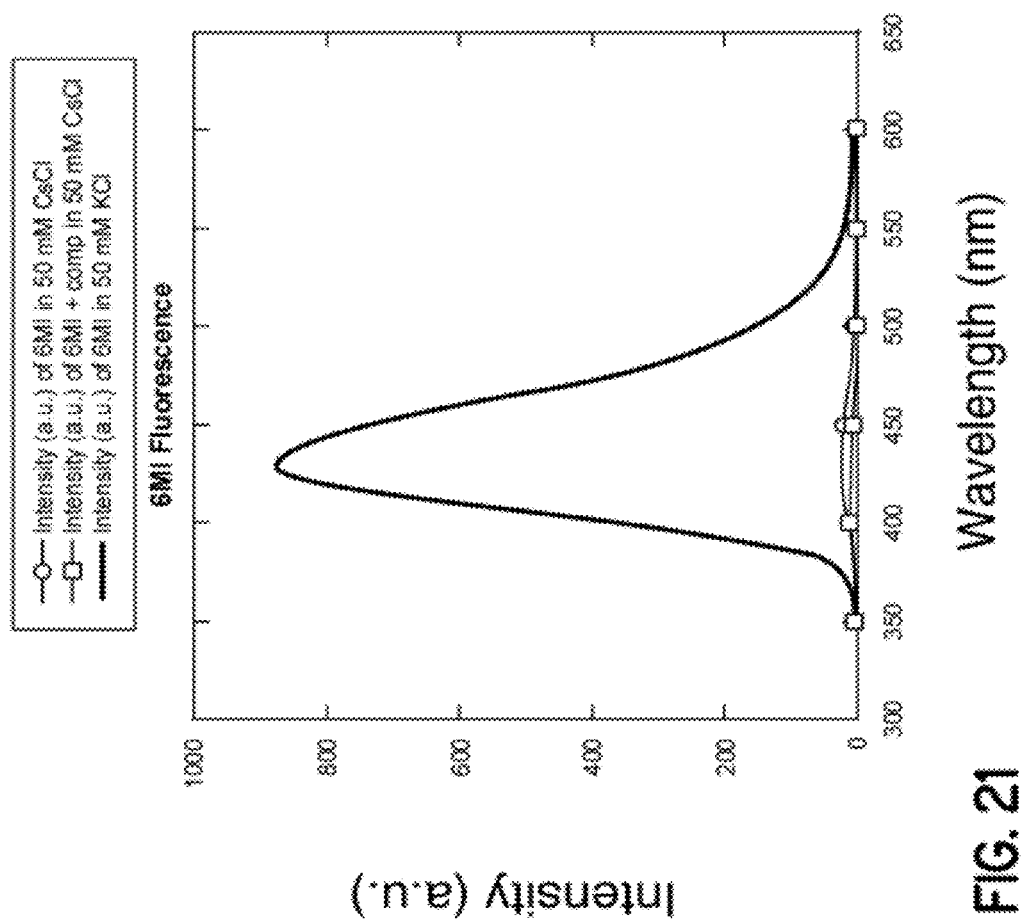
FIG. 21 is a graph of fluorescence spectra of GGG(6MI) GGGCGGGCGGG [SEQ. ID. NO. 21] without and with its complementary strand.

The reported NMR structure of $(GGGT)_4$ [SEQ. ID. NO. 1] [Jing, N. et al. (1998) Structure-activity of tetrad-forming oligonucleotides as a potent anti-HIV therapeutic drug. *J Biol Chem*, 273, 34992-34999] suggests that the quadruplex structure is monomolecular with opposite directions of G-tracts (anti-parallel conformation) (FIG. 9A). However, CD spectra collected by us and published [in Jing, N. et al. (2001) Structure-activity of inhibition of HIV-1 integrase and virus replication by G-quartet oligonucleotides. *DNA Cell Biol*, 20, 499-508 incorporated by reference herein in its entirety] suggest that all strands in the structure must be parallel [Lu, M. et al. (1993) Thermodynamics of G-tetraplex formation by telomeric DNAs. *Biochemistry*, 32, 598-601]. Previously performed UV melting experiments also agree that the structure is monomolecular and unusually stable [see Jing, N., et al. (1997) Ion selective folding of loop domains in a potent anti-HIV oligonucleotide. *Biochemistry*, 36, 12498-12505 incorporated by reference in its entirety]. Based on the thermal stability of $(GGGT)_4$, CD characteristics, and the monomolecular nature of the complex, it is hypothesized that three G-quartets are formed by diagonal single T-loops (FIG. 20, panel B). Our model is supported by the fact that deletion of the terminal T16, which is not involved in the parallel structure, did not reveal any destabilization (FIG. 6). In contrast, according to the anti-parallel conformation (FIG. 20, panel A), T16 is involved in quadruplex formation, and therefore its deletion should have a significant destabilization effect.

Incorporation of 2Ap at the 4th position fully restored its emission upon quadruplex formation (FIG. 7). The magnitude of the fluorescence effect can be explained by the fact that both adjacent guanines are immobilized in stable G-quartets without any possibility of quenching the fluorophore (FIG. 20, panel B). Since T8 and T12 form similar single-nucleotide loops, testing 2Ap in these positions is proposed to design an ultra-sensitive primer-probe of RT-QPA.

Alternative Strategies.

The hypothetical model of the parallel structure shown in FIG. 20, panel B is based on thermodynamic and spectroscopic studies. Three G-quartets were assumed because of higher thermal stability of the G3T quadruplex when compared with the quadruplexes with two G-quartets [Kankia, B. I. et al. (2001) Folding of the thrombin aptamer into a G-quadruplex with Sr(2+): stability, heat, and hydration. *J Am Chem Soc*, 123, 10799-10804; Hardin, C. C. et al. (2000) Thermodynamic and kinetic characterization of the dissociation and assembly of quadruplex nucleic acids. *Biopolymers*, 56, 147-194 incorporated by reference herein in their entireties]. However, one can't exclude two G-quartets in the G3T sequence with three diagonal GT loops. To test this possibility, substitution at positions 3, 7 and 11 will be made and studied for their effect on quadruplex formation. Depending on the outcome, incorporation of 2Ap in positions 3, 7 and 11 will also be tested.

Thus, the sensitivity of QPA probes may be further increased by incorporating more than one 2Ap within the loop regions of G3T-ss13 [SEQ. ID. NO. 12]. It is believed that the loop region is the most convenient location to avoid quenching from neighboring bases and reach the maximum emission of 2Ap. The reported NMR structure of $(GGGT)_4$. [SEQ. ID. NO. 1] [Jing, N. and Hogan, M. E. (1998) Structure-activity of tetrad-forming oligonucleotides as a potent anti-HIV therapeutic drug. The Journal of biological chemistry, 273, 34992-34999] suggests that the quadruplex structure is monomolecular with opposite directions of G-tracts (anti-parallel conformation) (FIG. 20, panel A). However, CD spectra collected by us (data not shown) and published earlier [Jing, N., Marchand, C., Guan, Y., Liu, J., Pallansch, L., Lackman-Smith, C., De Clercq, E. and Pommier, Y. (2001) *Structure-activity of inhibition of HIV-1 integrase and virus replication by G-quartet oligonucleotides*. DNA Cell Bid, 20, 499-508] suggest that all strands in the structure must be parallel [Lu, M., Guo, Q. and Kaltenbach, N. R. (1993) *Thermodynamics of G-tetraplex* formation by telomeric DNAs. Biochemistry, 32, 598-601]. UV melting experiments (not shown) also suggest that the structure is monomolecular and unusually stable [Jing, N., Rando, R. F., Pommier, Y. and Hogan, M. E. (1997) Ion selective folding of loop domains in a potent anti-HIV oligonucleotide. Biochemistry, 36, 12498-12505]. Based on the thermal stability of $(GGGT)_4$, [SEQ. ID. NO. 1] CD characteristics, and the monomolecular nature of the complex, it is believed that three G-quartets are formed by diagonal single T-loops (FIG. 20, panel B). This model is supported by the fact that deletion of the terminal T16, which is not involved in the parallel structure (FIG. 20, panel B), did not reveal any destabilization (data not shown). In contrast, according to the anti-parallel conformation (FIG. 20, panel A), T16 is involved in quadruplex formation, and therefore its deletion should have a significant destabilization effect. As shown in FIG. 7, incorporation of 2Ap at the 4th position fully restored its emission upon quadruplex formation. The magnitude of the fluorescence effect can be explained by the fact that both adjacent guanines are immobilized in stable G-quartets without any possibility of quenching the fluorophore (FIG. 20, panel B). Since T8 and T12 form similar single-nucleotide loops, 2Ap will be tested in these positions to design an ultra-sensitive primer-probe of RT-QPA.

Development of Pteridine-Containing QPA Probes.

As described above, it is possible to incorporate labels other than 2Ap into the primer sequence. Thus, to design QPA probes for multiplex testes, similar studies will be performed using highly fluorescent pteridine analogs 3-methyl isoxanthopterin (3MI) (Ex348, Em431), 6-methylisoxanthopterin (6MI) (Ex340, Em430) and (4-amino-6-methyl-8-(2¢-deoxy-â-D-ribofuranosyl)-7(8H)-pteridone (6AMP) (Ex330, Em435) with quantum yields of 0.88, 0.70 and 0.39 as monomer form, respectively. DNA containing pteridine probes is commercially available from Fidelity Systems. All three pteridine analogs show significant quenching upon incorporation into a DNA strand [Hawkins, M. E. (2008) *Fluorescent pteridine probes for nucleic acid analysis*. Methods in enzymology, 450, 201-231]. 6MI and 6AMP also show almost perfect base-pairing with cytosine and thymine, respectively. 3MI does not form stable base-pairs and its destabilization effect is similar to an effect of a single base-pair mismatch [Hawkins, M. E. (2008) *Fluorescent pteridine probes for nucleic acid analysis*. Methods in enzymology, 450, 201-231]. However, the analog will be studied due its highest quantum yield.

Product Quantification Using QPA.

After finding optimal experimental conditions and primers, QPA will be used to quantify DNA products in real-time. The amplification will be performed at various concentrations (from femtomolar to nanomolar) of DNA template. QPA will be performed on DNA templates with incorporated QPA-target sites obtained from the pUC18 plasmid (see Example 4). Initially, thermocycling QPA is planned. No product is expected at initial temperature cycles as the fluorescence signal will be below the detection threshold of the instrument (see FIG. 1). However, at threshold cycles an increase in fluorescence is expected. Observing a linear dependence between log of the starting amount of templates and the corresponding number of threshold cycles is also expected. Similarly, a linear dependence is expected upon isothermal QPA between log of the starting amount of templates and time.

In order to compare RT-QPA with current detection mechanisms, a molecular beacon probe with Fluorescein tag will be designed. In these experiments, thermocycling QPA will be monitored by two independent ways: 2Ap fluorescence at 370 nm (RT-QPA) and Fluorescein emission at 521 nM (molecular beacon). Earlier detection of DNA product by 2Ap signal relative to the molecular beacon signal is expected.

The embodiments of the present invention recited herein are intended to be merely exemplary and those skilled in the art will be able to make numerous variations and modifications to it without departing from the spirit of the present invention. Notwithstanding the above, certain variations and modifications, while producing less than optimal results, may still produce satisfactory results. All such variations and modifications are intended to be within the scope of the present invention as defined by the claims appended hereto.

What is claimed is:

1. A primer for amplification of a target nucleic acid, the primer comprising a first sequence segment and a second sequence segment;
   wherein the first sequence segment comprises a G-rich sequence corresponding to the formula $G_{3-3+}N_{1-7}G_{3-3+}N_{1-7}G_{3-3+}N_{1-7}G_{0-3}$, and wherein the G content of the G-rich sequence is equal to or greater than 70%; and
   wherein the second sequence segment is sufficiently complementary to the target nucleic acid to hybridize therewith, and wherein the first sequence segment does not hybridize to the second sequence segment or to a sequence of the target nucleic acid, and wherein the G-rich sequence of the first sequence segment conforms into a quadruplex conformation during an extension step of a polymerase chain reaction.

2. The primer of claim 1, wherein at least a portion of the first sequence segment has a sequence comprising $(GGGT)_4$ [SEQ ID NO: 1].

3. The primer of claim 1, further including in its sequence at least one label chosen from 2Ap, 3MI, 6MI, and 6AMP.

4. The primer of claim 3, wherein at least a portion of the first sequence segment has a sequence comprising SEQ ID NO: 10 which is labeled as GGG(2Ap)GGGTGGGTGGG.

5. The primer of claim 4, wherein the portion of the first sequence segment comprising 2Ap-G3T is attached to another sequence specific for use as a primer to detect a desired target nucleic acid sequence.

6. The primer of claim 1, wherein the portion of the first sequence segment having a sequence comprising $G_{3-3+}N_{1-7}G_{3-3+}N_{1-7}G_{3-3+}N_{1-7}G_{0-3}$ has a sequence chosen from SEQ ID NO: 1, SEQ ID NO: 2, SEQ ID NO: 10 which is labeled as GGG(2Ap)GGGTGGGTGGG, SEQ ID NO: 11 which is labeled as GGG(2Ap)GGGTGGGTGG, and SEQ ID NO: 12 which is labeled as GGG(2Ap)GGGTGGGTG.

7. A process for amplifying at least one target nucleic acid sequence contained in a nucleic acid or a mixture of nucleic acids, the process comprising:
   treating a nucleic acid or a mixture of nucleic acids with at least one primer, wherein at least a portion of the primer comprises a G-rich sequence corresponding to the formula $G_{3-3+}N_{1-7}G_{3-3+}N_{1-7}G_{3-3+}N_{1-7}G_{0-3}$, and wherein the G content of the G-rich sequence is equal to or greater than 70%, which allows the primer to conform into a quadruplex conformation during an extension step of a polymerase chain reaction, under isothermic conditions such that, for the at least one nucleic acid sequence being amplified, an extension product of the at least one primer is synthesized which is complementary to a strand from the nucleic acid or a mixture of nucleic acids,
   wherein the at least one primer is selected so as to be sufficiently complementary to the strand from the nucleic acid or a mixture of nucleic acids to hybridize therewith such that the extension product synthesized from the at least one primer, when it is separated from its complement, can serve as a template for further synthesis of an extension product of another primer.

8. The process of claim 7, further comprising separating the primer extension products from the templates on which they were synthesized to produce single-stranded molecules.

9. The process of claim 7, further comprising treating the single-stranded molecules with the at least one primer under isothermic conditions such that a primer extension product is synthesized using each of the single strands as a template.

10. The process of claim 7, wherein at least a portion of the primer sequence has a sequence comprising $(GGGT)_4$ [SEQ ID NO:1].

11. The process of claim 7, wherein the at least one primer further includes in its sequence at least one label chosen from 2Ap, 3MI, 6MI, and 6AMP.

12. The process of claim 11, wherein at least a portion of the primer sequence has a sequence comprising SEQ ID NO: 10 which is labeled as GGG(2Ap)GGGTGGGTGGG.

13. The process of claim 12, wherein the portion of the primer sequence comprising 2Ap-G3T is attached to another sequence specific for use as a primer to detect a desired target nucleic acid sequence.

14. The process of claim 7, wherein the portion of the primer comprising the G-rich sequence corresponding to the formula $G_{3-3+}N_{1-7}G_{3-3+}N_{1-7}G_{3-3+}N_{1-7}G_{0-3}$ has a sequence chosen from SEQ ID NO: 1, SEQ ID NO: 2, SEQ ID NO: 10 which is labeled as GGG(2Ap) GGGTGGGTGGG, SEQ ID NO: 11 which is labeled as GGG(2Ap)GGGTGGGTGG or SEQ ID NO: 12 which is labeled as GGG(2Ap)GGGTGGGTG.

15. A real-time quantification PCR method for detecting amplification of a target nucleic acid comprising:
   treating a nucleic acid or a mixture of nucleic acids with at least one primer, wherein at least a portion of the primer comprises a G-rich sequence corresponding to the formula $G_{3-3+}N_{1-7}G_{3-3+}N_{1-7}G_{3-3+}N_{1-7}G_{0-3}$, and wherein the G content of the G-rich sequence is equal to or greater than 70%, which allows the primer to conform into a quadruplex conformation during an extension step of a polymerase chain reaction, under conditions such that, for the at least one nucleic acid sequence being amplified, an extension product of the at least one primer is synthesized which is complementary to a strand from the nucleic acid or a mixture of nucleic acids;
   wherein the at least one primer includes at least one label that is quenched when the at least one primer is in a non-quadruplex conformation and that is detectable when the at least one primer is in a quadruplex conformation; and
   detecting the level of the label.

16. The method of claim 15, wherein the label is chosen from 2Ap, 3MI, 6MI, and 6AMP, and is incorporated into the at least one primer.

17. A primer for amplification of a target nucleic acid, the primer comprising a first sequence segment and a second sequence segment;
   wherein at least a portion of the first sequence segment comprises a sequence corresponding to the formula $G_{2-4}N_{1-3}G_{2-4}N_{1-3}G_{2-4}N_{1-3}G_{0-3}$, which allows the primer to conform into a quadruplex conformation during an extension step of a polymerase chain reaction; and
   wherein the second sequence segment is sufficiently complementary to the target nucleic acid to hybridize therewith, and wherein the first sequence segment does not hybridize to the second sequence segment or to a sequence of the target nucleic acid.

18. A primer for amplification of a target nucleic acid, the primer having a first sequence segment and a second sequence segment;
   wherein at least a portion of the first sequence segment has a sequence chosen from SEQ ID NO: 1, SEQ ID NO: 2, SEQ ID NO: 3, SEQ ID NO: 10 which is labeled as GGG(2Ap)GGGTGGGTGGG, SEQ ID NO: 11 which is labeled as GGG(2Ap)GGGTGGGTGG, SEQ ID NO: 12 which is labeled as GGG(2Ap) GGGTGGGTG, SEQ ID NO: 20 which is labeled as GGTTGG(2Ap)GTGGTTGG, and SEQ ID NO: 24 which is labeled as GG(2Ap)TGGTGTGGTTGG, which allows the primer to conform into a quadruplex conformation during an extension step of a polymerase chain reaction; and
   wherein the second sequence segment is sufficiently complementary to the target nucleic acid to hybridize therewith, and wherein the first sequence segment does not hybridize to the second sequence segment or to a sequence of the target nucleic acid.

* * * * *

UNITED STATES PATENT AND TRADEMARK OFFICE
CERTIFICATE OF CORRECTION

| | | |
|---|---|---|
| PATENT NO. | : 9,499,860 B2 | |
| APPLICATION NO. | : 13/579486 | |
| DATED | : November 22, 2016 | |
| INVENTOR(S) | : Besik Kankia | |

It is certified that error appears in the above-identified patent and that said Letters Patent is hereby corrected as shown below:

On the Title Page

Page 2,
Column 1, Line approx. 9, "ntramolecular" should be -- intramolecular --.

In the Drawings

Figure 4, "promer" should be -- primer --.
Figure 14, "Templat" should be -- Template --.

In the Specification

Column 2,
Line 6, "results" should be -- result --.
Line 56, "includes of a series" should be -- includes a series --.

Column 3,
Line 57, "TagMan®" should be -- TaqMan® --.

Column 4,
Line 10, "TagMan®" should be -- TaqMan® --.
Line 35, "TagMan®," should be -- TaqMan®, --.

Column 6,
Lines 56-57, "each of the primers used have" should be -- each of the primers used has --.

Signed and Sealed this
Twenty-second Day of August, 2017

Joseph Matal
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 9,499,860 B2

Column 10,
Line 6, "TagMan®," should be -- TaqMan®, --.
Line 16, "MgCl2," should be -- $MgCl^2$, --.
Line 44, "MgCl2," should be -- $MgCl^2$, --.

Column 12,
Line 24, "form" should be -- from --.
Lines 53-54, "each of the primers used have" should be -- each of the primers used has --.

Column 15,
Lines 43-44, "TagMan®" should be -- TaqMan® --.

Column 16,
Line 35, "TagMan®" should be -- TaqMan® --.
Line 39, "TagMan®." should be -- TaqMan®. --.
Line 40, "TagMan®" should be -- TaqMan® --.

Column 18,
Line 12, "10]" should be -- 10]. --.

Column 21,
Line 56, "primer," should be -- primer. --.

Column 22,
Line 12, "TagMan®," should be -- TaqMan®, --.
Line 15, "is" should be -- are --.

Column 31,
Line 31, "concentration)." should be -- concentration.) --.

Column 33,
Line 36, "incorporation" should be -- incorporating --.

Column 34,
Line 44, "substitution" should be -- substitutions --.

Column 36,
Line 7, "due its" should be -- due to its --.